United States Patent [19]
Case et al.

[11] Patent Number: 5,328,847
[45] Date of Patent: Jul. 12, 1994

[54] THIN MEMBRANE SENSOR WITH BIOCHEMICAL SWITCH

[76] Inventors: George D. Case, 17780 SW. Wright St., Aloha, Oreg. 97007; Jennings F. Worley, III, 3500 Swarthmore Rd., Durham, N.C. 27713

[21] Appl. No.: 794,734
[22] Filed: Nov. 18, 1991

Related U.S. Application Data

[63] Continuation-in-part of Ser. No. 481,213, Feb. 20, 1990, abandoned.

[51] Int. Cl.$^5$ .................. C12M 1/34; C12M 1/40; G01N 30/96; C25F 7/00
[52] U.S. Cl. .................. 435/291; 435/287; 435/288; 435/817; 422/68.1; 422/69; 204/153.12
[58] Field of Search ............ 422/68.1, 69; 435/291, 435/288, 287, 817; 204/403, 653.12

[56] References Cited

U.S. PATENT DOCUMENTS

| | | | |
|---|---|---|---|
| 3,966,580 | 6/1976 | Janata et al. | 204/403 |
| 4,214,968 | 7/1980 | Battaglia | 204/195 M |
| 4,343,782 | 8/1982 | Shapiro | 424/3 |
| 4,634,599 | 1/1987 | Uzgiris | 435/7 |
| 4,637,861 | 1/1987 | Krull et al. | 204/1 T |
| 4,661,422 | 4/1987 | Marianowski | 429/13 |
| 4,661,442 | 4/1987 | Lukens | 435/4 |
| 4,776,944 | 10/1988 | Janata et al. | 204/415 |

FOREIGN PATENT DOCUMENTS

| | | |
|---|---|---|
| 125554 | 11/1984 | European Pat. Off. . |
| 128318 | 12/1984 | European Pat. Off. . |
| 0149405 | 7/1985 | European Pat. Off. . |
| 231010 | 8/1987 | European Pat. Off. . |
| 248680 | 12/1987 | European Pat. Off. . |
| 0261887 | 3/1988 | European Pat. Off. . |
| 288256 | 10/1988 | European Pat. Off. . |
| 290269 | 11/1988 | European Pat. Off. . |
| 302661 | 2/1989 | European Pat. Off. . |
| 304947 | 3/1989 | European Pat. Off. . |
| 0304947 | 3/1989 | European Pat. Off. . |
| 3226045 | 1/1983 | Fed. Rep. of Germany . |
| 2614422 | 10/1988 | France . |
| 58-103659 | 6/1983 | Japan . |
| 60-44865 | 3/1985 | Japan . |
| 62-64941 | 3/1987 | Japan . |
| 62-85853 | 4/1987 | Japan . |
| 63-153462 | 6/1988 | Japan . |
| 63-171355 | 7/1988 | Japan . |
| 63-206652 | 8/1988 | Japan . |
| 63-263460 | 10/1988 | Japan . |
| 0159055 | 3/1989 | Japan . |

(List continued on next page.)

OTHER PUBLICATIONS

Lin, et al,. "Characterization of Immobilized Antibodies on Silica Surfaces," *IEEE Transaction on Biomedical Engineering*, vol. 35 (No. 6).

(List continued on next page.)

*Primary Examiner*—Robert J. Warden
*Assistant Examiner*—Christopher Y. Kim
*Attorney, Agent, or Firm*—Keck, Mahin & Cate

[57] ABSTRACT

A modular biosensor system for chemical or biological agent detection utilizes electrochemical measurement of an ion current across a gate membrane triggered by the reaction of the target agent with a recognition protein conjugated to a channel blocker. The sensor system includes a bioresponse simulator or "biochemical switch" module which contains the recognition protein-channel blocker conjugate, and in which the detection reactions occur, and a transducer module which contains a gate membrane and a measuring electrode, and in which the presence of agent is sensed electrically. In the poised state, ion channels in the gate membrane are blocked by the recognition protein-channel blocker conjugate. Detection reactions remove the recognition protein-channel blocker conjugate from the ion channels, thus eliciting an ion current surge in the gate membrane which subsequently triggers an output alarm. Sufficiently large currents are generated that simple direct current electronics are adequate for the measurements. The biosensor has applications for environmental, medical, and industrial use.

23 Claims, 10 Drawing Sheets

FOREIGN PATENT DOCUMENTS

| | | |
|---|---|---|
| 0159057 | 3/1989 | Japan . |
| 0159058 | 3/1989 | Japan . |
| 0160382 | 3/1989 | Japan . |
| 8703095 | 5/1987 | PCT Int'l Appl. . |
| 8808972 | 11/1988 | PCT Int'l Appl. . |
| 8809499 | 12/1988 | PCT Int'l Appl. . |
| 8809808 | 12/1988 | PCT Int'l Appl. . |
| 8901159 | 2/1989 | PCT Int'l Appl. . |
| 9002327 | 3/1990 | PCT Int'l Appl. . |
| 9008783 | 8/1990 | PCT Int'l Appl. . |
| 1189224 | 7/1983 | U.S.S.R. . |

OTHER PUBLICATIONS

Krull, et al, "Langmuir–Blodgett Technology and Receptor Action in Stabilized Lipid Membranes," in *Fundamentals and Applications of Chem.*

Janata, et al, "Chemical Sensors," *Analytical Chemistry*, vol. 60, pp. 62R–74R, 1988 Zin particular pp. 67R–68R).

Wohtjen, "Chemical Microsensors and Microinstrumentation," *Analytical Chemistry*, vol. 55: pp. 98A–108A, 1984.

Krull, "Ion–Current Signal Optimization for Lipid Membrane Based Biosensors," *Analytical Chimica Acta*, vol. 192: pp. 321–326, 1987.

Fritsche, "Clemiluminescence Method for the Determination of Nanogram Amounts of Highly Toxic Alkylphosphates," *Analytica Chimical Acta*.

Case, "Magnetic Resonance Studies of the Mitochondrial Divalent Cation Carrier," *Biochiemica et Biophysica Actas*, vol. 375: pp. 69–86.

Caras, et al, "Enzymatically Sensitive Field Effect Transistors," *Methods in Enzymology*, vol. 137: pp. 247≧255, 1988.

Neher, et al, "Single–channel currents recorded from membrane of denervated ffog muscle fibers," *Nature*, vol. 260: pp. 799–802, 1976.

DeFelice, *Introduction to Membrane Noise*, pp. 386–407, Plenum Press, 1981.

Feher, et al, "Fluctuation Spectroscopy: Determination of Chemical Reaction Kinetics from the Frequency Spectrum of Fluctuations," *Proc. N.* Stryer, *Biochemistry* (3rd Ed.), pp. 288–293 and 964–969 Freeman.

Urban, et al, "Ion Movements in Gramicidin Pores: An example of Single–File Transport," (*Biochimica et Biophysica Acta*), vol. 602: pp. 331–354.

Shi, et al, "Action of calcium channel and beta–adrenergic blocking agents in bilayer lipid membranes," *Biochimica et Biophysica Acta*, vol. Clicheportiche et al., "Synthesis of new, highly radioactive tetrodotoxin derivatives and their binding properties to the sodium channel,".

Krueger, et al, "Block of sodium channels in planar lipid bilayers by guanidium toxins and calcium": Are the mechanisms of voltage dependence.

Montal et al., "Channel properties of the purified acetylcholine receptor from T. Californica reconstituted in planar lipid bilayer membranes".

Angelides et al., "Spatial relations of the neurotoxin binding sites on the sodium channel," Ann. N.Y. Acad. Sci. 221 (1987).

Hub et al., "Polymerization of lipid and lysolapid like diacetylenes in monolayers and liosomes," J. Macromol. Sci.–Chem. A15(5):701–715 (1981).

Krull et al., "Langmuir–Blodgett film characteristics and phospholipid membrane ion conduction," Analytica Chimica Acta 174:83–94 (1985).

THIN MEMBRANE SENSOR WITH BIOCHEMICAL SWITCH

This invention was made with Government support under contract Nos. NAS8-38470 and NAS8-38965 awarded by NASA, and Contract No. F33615-90-C-0605 awarded by the U.S. Department of the Air Force. The Government has certain rights in this invention.

This is a continuation-in-part of U.S. patent application Ser. No. 481,213, filed Feb. 20, 1990, now abandoned.

FIELD OF THE INVENTION

This invention relates to the detection and monitoring of the presence of biological agents and immunogenic chemical substances, for foodborne, waterborne, and airborne contamination verification, and the exposure or risk of exposure of persons to such agents or materials in their work environment, and is concerned more particularly with a simple method of achieving such detection which can be embodied into a small portable element, for example, as a badge or test chip, which can be self-contained and direct acting, thereby providing a prompt indication of exposure.

A biosensor method to detect quickly the minute presence of chemical or biological agents offers significant promise for early warning hazard evaluation or rapid process or system control. Transduction of the sensing reactions into an electronic readout in this system by means of a biochemical switch is facilitated by the present invention. The present invention offers potential as a portable, miniaturized "first alert" biosensor alarm for chemical or biological materials. Its usefulness is anticipated for laboratory, industrial, or field applications such as detection of environmental pollutants, chemical or biological substances, botulinum toxin detection in food packaging, spoilage indication, pathogen detection in water treatment, biological screening for hepatitis or HIV products or the like, rapid detection of microorganisms or toxins, and detection of fugitive pharmaceutical materials.

BACKGROUND OF THE INVENTION

Prior art methods for high-sensitivity detection of chemical and biological materials have typically relied on colorimetric or electrometric analyses of enzymatic or immunological reactions of the test analytes. Enzyme immunoassay (EIA) techniques have been incorporated into a large number of biosensor devices employing colorimetric or fluorimetric analyses, as exemplified in the following U.S. and foreign patents: U.S. Pat. No. 4,343,782; EP 125,554; EP 128,318; EP 231,010; EP 288,256; EP 290,269; SU 1,189,224; JP 57,208,457. In a typical embodiment, an enzyme-conjugated antigen admixed with immobilized antibody reacts competitively with free test antigen to release the enzyme into solution containing its substrate, and subsequent enzyme reaction products are detected by changes in color or fluorescence. A drawback of this method is background color which limits sensitivity.

U.S. Pat. No. 4,343,782 to Shapiro, issued Aug. 10, 1982, describes a cytological assay procedure for non-excitable cells in which their membrane potential measured by an optical property of a permeant dye is used to determine characteristics of individual cells. Japanese Patent No. 57,208,457 to Olympus Optical Co., Ltd., published Dec. 21, 1982, describes an automated apparatus for staining of cells or tissues, including an indicator installed for the determination of dye concentration.

European Patent No. 125,554 to Charlton, published Nov. 21, 1984, describes an ion test means having a hydrophilic carrier matrix, which consists of a hydrophilic carrier matrix loaded with hydrophobic globules containing an ionophore, and a reporter substance and titanium dioxide, in a test strip attached to a support. European Patent No. 128,318 to Charlton et al., published Dec. 19, 1984, describes the use of substituted indonaphthols as reporter substances in detecting ions in ionophore-containing test strips, for the detection of ions in aqueous solutions. U.S.S.R. Patent No. 1,189,224 to Lemeshko and Brovkovich, published Jul. 26, 1983, describes a method of determining phospholipids in biological membranes, by treating the preparations with chloroform-methanol and a molybdenum color reagent. European Patent No. 231,010, to Halsey et al., published Aug. 5, 1987, describes a method of solid phase enzyme immunoassay and nucleic acid hybridization assay, in which a chromogenic material upon changing color in the presence of a solid phase enzyme, binds to the solid phase. Color change is analyzed on a dip stick, for use in allergy testing. European Patent No. 288,256, to Toner, published Oct. 26, 1988, describes europium chelates with polypyridine and phenanthroline derivatives for fluorescent labels for immunoassays.

Electrochemical coupling of EIA permits direct electronic readout, but may suffer from similar sensitivity limitations. Examples of prior art methods are disclosed in the following U.S. and foreign patents: U.S. Pat. No. 4,214,968; JP 58,103,659; JP 60, 44,865; JP 62,64,941; JP 63,171,355; JP 63,263,468; EP 302,661. U.S. Pat. No. 4,214,968 to Battaglia et al., issued July 29, 1980, describes a dry operative ion selective electrode comprising a dried salt solution in a hydrophilic polymeric binder in the internal reference, in contact with a hydrophobic ion-selective membrane containing an ion carrier dissolved therein.

Japanese Patent No. 60,44,865 to Fuji Photo Film Co., Ltd., published Mar. 11, 1985, describes a multilayered analytical element for ammonia determination in body fluids comprising a water-resistant support coated with an ammonia indicator layer, a barrier layer which is permeable to ammonia but not to liquid substances, a reagent layer which transforms ammonia-forming substances to ammonia, and a porous spreading layer. Japanese Patent No. 58,103,659 to Toshiba Corp., published Jun. 20, 1983, describes membranes for ion-selective electrodes, including a tetrahydrofuran solution of valinomycin dispersed in polyvinyl chloride in the presence of dioctyl phthalate and potassium tetraphenylboron, dried into a membrane useful for the determination of ions in blood. Japanese Patent No. 63,171,355 to Tsukada et al., published Jul. 15, 1988, describes a semiconductor chemical sensor for blood analysis, in which the surface of a field effect transistor gate on a base is coated with a hydrophilic polymer membrane and the membrane is treated with electrically accelerated particles to form hydrophilic groups.

Japanese Patent No. 62,64,941 to Takei et al., published Mar. 24, 1987, describes enzyme-immobilized membranes for a sensor, in which high molecular weight substances are dissolved, the mixture spread and air dried, and soaked in a solvent in which the high molecular weight component is insoluble, for enzyme immobilization. Japanese Patent No. 63,263,460 to Mitsumata et al., published Oct. 31, 1988, describes an immunoassay method using an enzyme immunosensor electrode, in which an electrode containing immobilized antibody is inserted into an electrolyte solution, enzyme-labelled antigen and a test antigen are added for competitive reaction with antibody, and instantaneous current or potential changes measured for detection of the antigen. European Patent No. 302,661 to Vadgama et al., published Feb. 8, 1989, describes a supported liquid membrane enzyme electrode sensor for analyte determination.

Biosensors incorporating electrochemical detection with adsorbed, deposited, or embedded receptor agents on an electrode are exemplified in the following U.S. and foreign patents: U.S. Pat. No. 4,634,599; U.S. Pat. No. 4,661,442; JP 63,153,462; JP 63,206,652; JP 01,59,058; EP 304,447; WO 87,03,095; WO 88,08,972; WO 88,09,499; and WO 88,09,808. In these systems, analyte detection is typically followed by a change in electrical potential or current at an electrode surface. Sensitivity and selectivity for specific analytes depend on the nature of the materials used on the electrode, and have limited the applicability of these devices.

Japanese Patent No. 63,153,462 to Takei et al., published Jun. 25, 1988, describes a sensitive field effect transistor biosensor containing an aluminum gate-immobilized biological substance. European Patent No. 304,947 to Kagayama, published Mar. 1, 1989, describes a biosensor containing immobilized physiologically active substance and transducer, comprising a pair of opposing flat plates between which an antibody, with antigen or enzymes immobilized onto one surface and a transducing chemical substance on the other surface.

PCT International Application No. WO 88,08,972 to Cheung et al., published Nov. 17, 1988, describes a biosensor comprising a reversibly selective binding protein immobilized upon the insulated gate region of a field effect transistor on the sensor. PCT International Application No. WO 88,09,808 to Taylor and Marenchic, published Dec. 15, 1988, describes receptor-based biosensors and a method of immobilizing and stabilizing an active biological receptor in a polymeric film onto an electrode. PCT International Application No. WO 88,09,499 to Newman, published Dec. 1, 1988, describes an optimized capacitive sensor for chemical analysis, which relies on biospecific binding between a biochemical binding system and the analyte of interest to change the dielectric properties of a capacitive affinity sensor.

Japanese Patent No. 01,59,058 to Kuriyama, published Mar. 6, 1989, describes an enzyme immunosensor and its use in enzyme immunoassay, consisting of a semiconductor ion sensor, a spacer, and plate containing immobilized antigen or antibody. French Patent 2,614,422 to Liston et al., published Oct. 28, 1988, describes an enzyme electrode and module for determination of analytes in physiological fluids, comprising a membrane chamber and composite layered membrane, an electrode element in contact with the membrane, a flow sampler connected with the membrane chamber, a wash cell and a sample container, and means for intermittent transfer of sample and sample and other solutions. German Patent No. 3,226,045 to Seshimoto et al., published Jan. 20, 1983, describes film-like ion selective electrodes comprised of a conductive layer adjacent to an ion-selective layer, and their use for body fluid analysis.

PCT International Application No. WO 87,03,095 to Newman, published May 21, 1987, describes a capacitive affinity sensor and method for chemical analysis and measurement, comprising an open capacitor which produces a higher electric field in one volumetric region and a lower field in a second region, a biospecific binding agent for the analyte localized on the surface between the conductors in the first region, and a means associated with the capacitor which responds to the average dielectric constant in the first chamber. U.S. Pat. No. 4,634,599, to Uzgiris, issued Jan. 6, 1987, describes a method for making ordered monolayers of macromolecules on supported lipid polylayers, for two-dimensional crystallization of macromolecules for imaging in electron microscopy. U.S. Pat. No. 4,661,442, to Lukens, issued Apr. 28, 1987, describes a process for preparing lipid-protein membranes for chemical detection, comprising an aqueous medium containing emulsified lipid and protein, applying the medium to an orifice, and evaporating the water to provide a stable membrane.

Membrane electrode biosensors incorporating oxidative probes, such as those used to detect glucose in blood, are exemplified in the following patents: FR 2,614,422; EP 248,680; JP 62,85,853; JP 01,59,055; JP 01,60,382. In these systems, a Clark-type oxygen sensing electrode is typically coupled to an oxidative enzyme such as glucose oxidase, in order to permit analysis of the desired biological parameter. Among other factors, synthetic membranes used in said systems vary in composition among the biosensor devices.

Japanese Patent No. 01,60,382 to Asakura, published Mar. 7, 1989, describes the manufacture of a fibroin-enzyme membrane and its use in an enzyme sensor. Japanese Patent No. 01,59,055 to Suetsugu et al., Mar. 6, 1989, describes water-absorbing layers in biosensors, for electrochemical detection of substances based on a reaction with a redox enzyme and an electron acceptor. Japanese Patent No. 62,85,853 to Miyai and Asano, published Apr. 20, 1987, describes a membrane for an enzyme electrode, comprised of an enzyme such as glucose oxidase immobilized on a fine powder carrier and supported with a membrane having a fractionating molecular weight capable of passing the protein molecule of the immobilized enzyme.

European Patent No. 248,680 to Reinhart et al., published Dec. 9, 1987, describes a noninvasive electrochemical apparatus and method for determining blood glucose, comprising a membrane means for containing glucose oxidase, means for providing oxygen to the membrane, and means for measuring the hydrogen peroxide product in the membrane.

Sensors using gated membrane electrodes, in which a reactive material for the analyte of interest is included in a membrane whose permeability changes upon reaction with the analyte, are exemplified in the following U.S. and foreign patents: U.S. Pat. No. 4,637,861; U.S. Pat. No. 4,776,944; and EP 261,887. Their sensitivity and selectivity are determined by the gated membrane composition, and can limit the types of agents which one can analyze by these methods. Activity of the gate material in prior art membranes can be strongly influenced by subtle physical changes in the membrane. For example, Krull, U. J., M. Thompson, E. T. Vandenberg, and H. E. Wong (1985) "Langmuir Blodgett Film Characteristics and Phospholipid Membrane Ion Conduction," *Analytica Chimica Acta* 174: 83–94; 95–102, describe packing density effects and capacitance measurements on electrodes with phospholipid membranes. Other influences include regulatory substances. For example Montal, M. P. Labarca, D. R. Fredkin, B. A. Suarez-Isla, and J. Lindstrom (1984) "Acetylcholine Receptor from Torpedo californica Reconstituted in Planar Lipid Bilayer Membranes," *Biophysical J.* 45: 165–174, describe effects of bungarotoxin and other ion channel modulating toxins in phospholipid membranes. See also Krueger, B. K., J. F. Worley, and R. J. French (1986) "Block of Sodium Channels in Planar Lipid Membranes by Guanidinium Toxins and Calcium: Are the Mechanisms of Voltage Dependence the Same?" *Annals of the New York Academy of Sciences* 479: 257–268).

Caras and Janata, "Enzymatically Sensitive Field Effect Transistors," *Methods in Enzymology,* Volume 137: pages 247–255, 1988, describes the design, fabrication, principles of operation, applications and theoretical limitations of enzymatically coupled field effect transistors as solid state biosensors.

SUMMARY OF THE INVENTION

The ultimate objective of the present invention is to provide a modular electrochemical biosensor for chemical and biological target agents, which incorporates a reaction between the target agent of interest and a recognition biomolecule in a biochemical switch module coupled with a gated membrane electrode in an indicator module. The membrane may contain any suitable combination of lipids, long-chain ($C_{12}$–$C_{24}$)organic compounds, plastic materials or like polymers for physical reinforcement. An additional object is to provide a compact, economical, easily portable, self-contained sensor which can be adapted in manufacture for a variety of chemical or biological agents.

Thus, according to the invention, an electrochemical biosensor for chemical or biological target agent detection is comprised of a bioresponse simulator, which is a biochemical switch module containing in film form a recognition biomolecule to which is conjugated an ion channel blocker moiety which controls ion permeation in a gate membrane; a gate membrane containing ion channels as a gate material which is sensitive to the channel blocker; and a measuring device comprising an electrode, which measures ion current changes across the gate membrane. In preferred embodiments of the invention, the recognition biomolecule comprises a protein including or conjugated to a recognition moiety, or a peptide or cell fragment. The recognition moiety may be a hapten, a nucleic acid fragment, or a receptor for the target agent of interest. In especially preferred embodiments, the recognition biomolecule is an albumin or an immunoglobulin type antibody. The channel blocker which blocks ion permeation is preferably a polyvalent cation, such as dysprosium, gadolinium or another trivalent lanthanide, or ruthenium red conjugated to the recognition moiety. The ion channel blocker can also be a guanidinium derivative covalently linked to the recognition moiety, or a conjugated complex metal ion such as ruthenium red.

The gate membrane contains a thin membrane, preferably of molecular monolayer or bilayer dimensions, in either fluid form or solid form, and in a preferred embodiment, the gate material is a gramicidin antibiotic producing gramicidin channels embedded therein. The membrane consists of hydrophobic plastic materials alone, or in combination with lipids, which impart both the structure necessary for gate material function and the physical strength necessary to operate in a biosensor. In preferred embodiments, the membrane contains a mixture of an acrylic polymer such as polylaurylmethacrylate with phosphatidylethanolamine and phosphatidylserine or similar phospholipids or fatty acid derivatives, or a mixture of a carboxylated polyacrylamide with minor amounts of surfactant and antibiotic activity such as that marketed by Rohm & Haas as a pressure-sensitive adhesive under the trade name "RHOPLEX N580" with or without similar lipids. The membrane may also include styrenepolyvinylpyridine copolymers.

The gated membrane and measuring device may be produced separately as an indicator module, to which the biochemical switch is applied prior to use.

DETAILED DESCRIPTION

Figure 1:
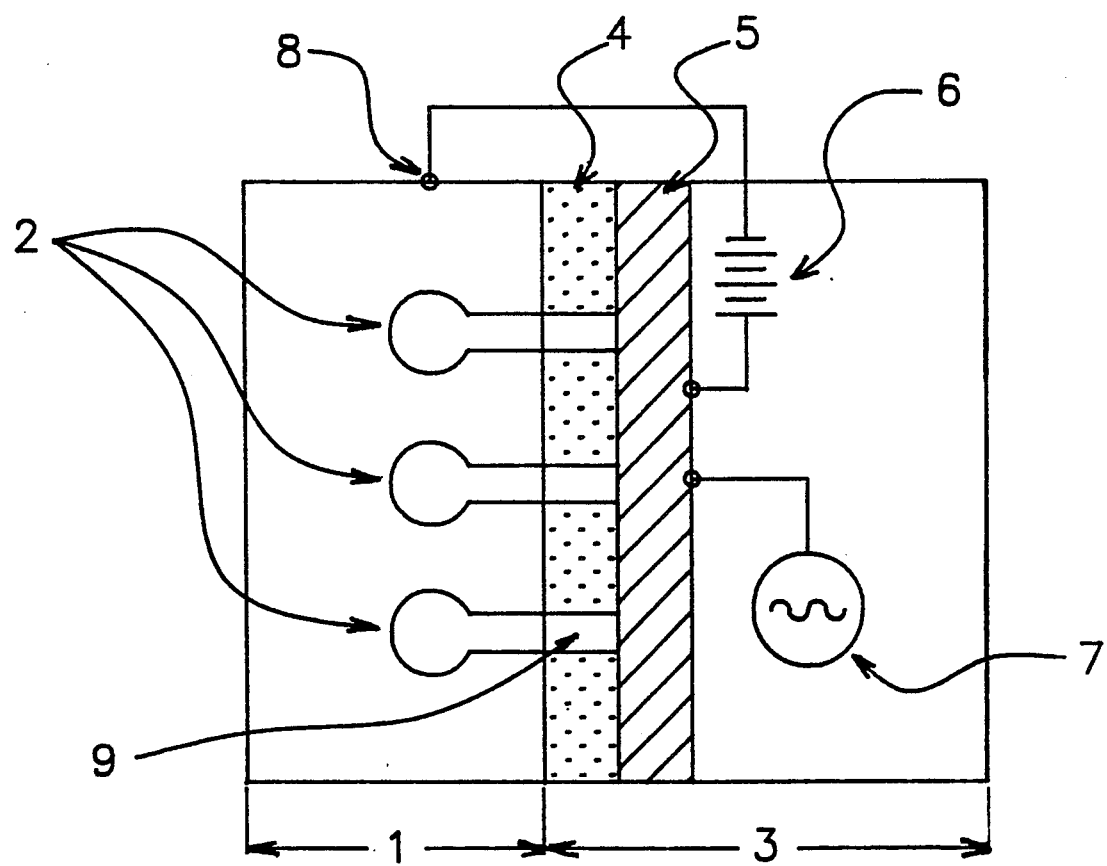
FIG. 1 is a schematic view of the biosensor in the poised state.

FIG. 1 shows a schematic view of the biosensor system, including the bioresponse simulator module functioning as a biochemical switch 1 with the recognition biomolecule 2 and an indicator module 3 with the gated membrane 4 affixed to a conductive measuring surface electrode 5. A self-contained direct current voltage source 6 and an indicator means output 7 are connected in a biosensor circuit by means of a poised polarizing electrode 8, contacted with the biochemical switch. The individual components as shown in FIG. 1 are exaggerated for visual clarity, and are not dimensionally to scale.

In the poised state, the recognition material conjugated to a channel blocker 2 is bound to the gate material creating ion channels 9 in the membrane 4 in such a manner as to effectively block ion permeation through the ion channels 9. Exposure of the sensor to a chemical or biological target agent elicits a reaction with the recognition material conjugated to the channel blocker 2, pulling it away from the gate material and enabling an ion current to flow across the membrane 4. This system thus functions as a biochemical switch. The resulting current surge is sensed at an electrode surface 5 in the transducer 3, triggering an alarm signal or other indicator response. Unlike prior art methods, such as U.S. Pat. Nos. 4,637,861 and 4,776,944 and European Patent appl. 304,947, in which selectivity enabling detection of chemical or biological agents is contained together with the ion channels, the present invention utilizes for detection selectivity a target agent-recognizing biomolecule conjugated to a common channel blocker in a biochemical switch module.

Provision of a reversible channel blocker is a novel feature of the present invention, which among other things enables sensor regeneration by replacing the outer liquid layer comprising the bioresponse simulator 1. An additional inventive feature is the ability to use a single common gate membrane composition for all classes of analytes. The gate membrane composition is designed to maximize current flow in the exposed state, thus simplifying the polarizing and detection electronic components relative to prior art methods cited above.

The biochemical switch module 1 generally consists of a hydrophilic film forming layer containing in a buffer solution of substantially neutral pH a recognition biomolecule for the target agent to which is conjugated a channel blocker substance which prevents ion permeation through the gate membrane 4. The layer may be stabilized by gelatin or the like. Examples of the recognition biomolecule include proteins such as immunoglobulin type antibodies or albumins which may or may not (depending on the desired target agent) have attached thereto a hapten or a nucleic acid segment or a protein segment. Thus, immunoglobulin (IgG, IgM, etc.) type antibodies are useful for the detection of specific antigens of interest. Chemically attached immunoglobulins or albumins are useful for the detection of specific antibodies of interest, or specific genetic material fragments, or the like. Methods for covalent attachment of haptens and nucleic acid derivatives to proteins such as immunoglobulins and albumins are well known and conventionally available (e.g., European Patent appl. 149,405, in which bifunctional fixation with glutaraldehyde effects the attachment.).

Channel blocker materials include bulky cations such as guanidinium compounds, and divalent or polyvalent cations. Examples of the former include agents such as tetrodotoxin and saxitoxin, and also neurotoxic organic derivatives such as tetramethylguanidine. Conjugation methods for guanidinium toxins have been described by Chicheportiche et al. (1980) *European J. Biochemistry* 104: 617–623.

A tetrodotoxin molecule may be covalently associated with a protein such as serum albumin by Pfitzner-Moffatt oxidation of tetrodotoxin alcohol function, Schiff-base formation with tritiated amines, and reduction of the imino-function by $NaCNBH_3$. In the first step, tetrodotoxin is reacted with a 5:1 molar excess of dicyclohexylcarbodiimide in anhydrous dimethylsulfoxide containing 10 mM $H_3PO_4$ catalyst for 3–4 hours at 40° C. The reaction can be verified by the appearance of dicyclohexylurea or by a positive 2,4,-dinitrophenylhydrazine test. The tetrodotoxin oxidation product is then reacted with an organic amine or amino acid in the presence of 12 mM $NaCNBH_3$ in 20% aqueous methanol for 24–48 hours at 100° C., to give a covalently conjugated tetrodotoxin-amino derivative.

An immunoglobulin-gadolinium complex of the present invention may be prepared as follows or in the appropriate manner. An immunoglobulin type antibody directed against one or more specific antigens, isolated and purified by means of methods conventionally known in the art, is concentrated by conventional means to a concentration of at least 0.01 mM (for example, 4–10 mg protein/mL). The solution is titrated volumetrically with 1 mM $GdCl_3$ in 5 mM imidazole buffer (pH = 7.0) to a molar stoichiometry on the order of 1:1. Binding of gadolinium to the immunoglobulin protein is verified spectrophotometrically, by mixing one volume of 1 mM murexide to 100 volumes of the 0.01 mM Gd-IgG complex solution, and comparing its visible spectrum in the region of 470 nm versus 540 nm against a comparable spectrum for free murexide alone. Typically, under these conditions, the difference is indistinguishable from zero. The Gd-IgG complex is thus ready for use in the invention.

The antibody may also be dissociated by methods conventionally known in the art into light chain subunits ("IgG-L") and heavy chain subunits ("IgG-H"), and the two subunit fractions separated and collected. The heavy chain H solution is titrated volumetrically with 1 mM $GdCl_3$ in 5 mM imidazole buffer (pH=7.0) to a molar stoichiometry on the order of 1:1, and verified as above. The Gd-IgG-H complex is then admixed with the light chain (IgG-L) solution to reconstitute the active antibody into the blocker-conjugated recognition biomolecule of the invention. This operation prevents the formation of lanthanide-light chain conjugates, thus decreasing the proportion of channel blockers that are not conjugated with the recognition moiety.

Examples of divalent or polyvalent cations useful as channel blockers include the divalent cations Ca(II), Sr(II), Ba(II), Cd(II), among others; and trivalent lanthanide cations such as La(III), Eu(III), Dy(III), Gd(III), and the like; and complex ions such as ruthenium red. Lanthanides as a class are well known to act similarly. Polyvalent cations, particularly the lanthanides, are preferred because of their substantially greater affinity as channel blockers. Effective blockage is achieved at concentrations some three orders of magnitude lower than for the divalent cations. Conjugation of lanthanide ions to the protein moiety may occur via coordination bonding, and may be performed in aqueous buffer solutions or while the cation is bound to ion channels in the gate membrane. In the latter case, the channels remain blocked. Reaction of the recognition protein-conjugated channel blocker with the analyte of interest at the ion channel site in the gate membrane results in removal of the blocker from the ion channel, and the onset of an ion current.

Ion channels conductive to monovalent or polyvalent ions serve as the gate material in the gate membrane 4. Examples include physiological sodium channel proteins, acetylcholine receptor protein, physiological calcium channel proteins, and channel-forming antibiotics such as the gramicidins (i.e., gramicidins A, A', D or S)

Gramicidins are advantageous because of their high conductance, stability, ease of handling, high loading capacity and availability.

In a gate membrane, gramicidin D forms two types of channels having different conductance. The channels are formed by dimers of two gramicidin D monomers. A monomer could form a channel in a monolayer membrane. Gramicidin S also forms ion channels but has a different structure from gramicidin D, and different sensitivity to channel blockers.

Physiological membranes containing ion channels can be used directly, and possess the advantage of being functional without any requirement for isolation or insertion for reconstitution into sensor membranes. As one example, cell membranes of viable bacteria can be fused directly into the sensor, to detect viability in the presence of dead cellular debris. In this case, the endogenous $-70$ mV potential associated with viable cells serves to drive the ion current detected by the sensor (the poising potential of the sensor being set otherwise near 0 mV). The live bacteria serve as a biochemical switch and provide gates for a hydrophobic membrane, and a voltage source for the measuring device.

Alternatively, ion channels can, in some cases, be inserted from solution phase into artificial membranes previously prepared using conventional Langmuir-Blodgett techniques, or by vesicle transfer, or by direct adsorption or absorption. If gramicidins are selected, one can use either monolayer or bilayer membrane structures. Lipid bilayers containing hundreds, and even thousands, of channels (either gramicidin D or gramicidin S) within a pinhole area have been observed, conducting ion currents potentially as high as 0.1–1.0 $mA/cm^2$. Preferably, gramicidin channels can be formed during preparation of the membrane, thus obviating the later insertion step.

The gate membrane consists of a hydrophobic material which is essentially impermeable to ions, particularly monovalent cations. Membranes can be prepared from phospholipids, or from polymerizable unsaturated organic compounds such as diacetylenic fatty acid derivatives, as in Hub, H. H., B. Hupfer, H. Koch, and H. Ringsdorf (1981) "Polymerization of Lipid and Lysolipid Like Diacetylenes in Monolayers and Bilayers," *J. Macromolecular Science—Chemistry* A15: 701–715, or the like.

Polymerizable lysophospholipid, phospholipid-like monomers, and phospholipid analogs containing diacetylene, butadiene or vinyl moieties are synthesized, where diacetylene moiety is the polymerizable unit. Monolayers of fatty acid or alcohol derivatives with simple ammonium, ether, amine, or phosphorus containing head groups are spread from chloroform solutions at the gas-water interface. Liposomes are prepared by sonication of aqueous suspensions of the monomers in water under nitrogen at 50° C. Polymerization is achieved by irradiation of these solutions with multichromatic light (Hg high pressure lamp) at 18° C. with an energy of 5 $mW/cm^2$ at the water surface under nitrogen. The UV initiated polymerization is a topochemical reaction and does not take place in solution. Formation of polymeric monolayers or liposomes from the diacetylenic monomers is indicated by a color change from colorless via blue to red, and is also established by their enhanced stability. Polymer liposomes are stable for months, cannot be destroyed by organic solvents, and can be viewed by scanning electron microscopy.

Plastic materials, either alone or in combination with lipids, may be used in the thin membrane of the present invention. Examples of plastic membrane compositions include polyvinylpyridine copolymers, or in preferred embodiments acrylic polymers such as polylauryl methacrylate, or a carboxylated acrylamide polymer such as a latex marketed under the trade name "RHOPLEX N580." Membranes can be prepared by Langmuir-Blodgett techniques, or by capillary thinning across an orifice separating two fluid phases in electrical contact with the sensor electrodes, or by evaporative or centrifugal thinning onto an electrode surface.

In the present invention, it is envisioned that conventional microelectronic configurations will serve adequately to supply power for the sensor, provide a constant direct current voltage in the poised state, and measure the ion current surge following an exposure trigger. For example, a conventional battery powered voltage source supports both the poised potential and the measuring electrode. (Configurations such as those conventionally used in digital watch displays and audible alarms may suffice.) The triggered current is anticipated to greatly exceed any base level ion current resulting from electrode bias.

Additionally, it may be desirable to incorporate into the detection electronics a provision for membrane integrity determination, based on the electrical noise accompanying a triggered current signal. The appearance of opening and closing events of ion channels in membranes as rapid fluctuations in membrane current is well known, and can be measured either in time domain or, as its Fourier transform, in frequency domain. In time domain, as exemplified by E. Neher and B. Sakman (1976) "Single-Channel Currents Recorded from Membrane of Denervated Frog Muscle Fibers," *Nature* 260: pp 799–802, fluctuation noise due to ion channel activity is identified by a periodic frequency histogram of incidents. Periodicity would be absent in a ruptured membrane. For a highly loaded membrane, the noise envelope is autocorrelated, or averaged, to verify open ion channel events as the origin of the triggered electric current signal. In frequency domain, as exemplified by G. Feher and M. Weissman (1973) "Fluctuation Spectroscopy: Determination of Chemical Reaction Kinetics from the Frequency Spectrum of Fluctuations," *Proc. Nat. Acad. Sci. U.S.* 70: pp 870–875, a small AC voltage component is overlaid upon the DC voltage at which the system is poised. Fluctuation noise is then determined as a function of the AC frequency. In the present invention, absence of (frequency-dependent) noise is suggestive of membrane rupture.

For purposes of further illustrating the embodiments of the current invention set forth above and in the following examples, quantitative ranges for various parameters can be provided to assist those of skill in the art in practicing the invention. It should be understood that the numerical ranges are illustrative, and not necessarily restrictive, because there are many variables which can be adjusted to achieve the desired result of sensitivity to a target agent.

With respect to the gate material, the number of channels per $mm^2$ membrane area may be in the range of from about 50 to about $10^9$ for gramicidin D and gramicidin S. There are two preferred ranges. The lower range of about 300 to about $10^3$ is preferred for configurations in which a simultaneous noise analysis measurement is desired in the detection electronics. The upper range of about $3 \times 10^4$ to about $10^6$ is preferred for embodiments in which simplicity is more important in the measurement electronics. Ion channel loading density is quadratically proportional to nominal concentration of the antibiotic. For example, 4 nM gramicidin (i.e., $4 \times 10^{-6}$ mM) gives a channel density of about 60/mm$^2$ but 300 nM gives a channel density of approx. 35,000/mm$^2$.

With regard to other channels, such as the calcium channel, the sodium channel, or the acetylcholine channel, the same ranges are appropriate. The upper limit of the broad range corresponds to a packing density on the order of 1% of the total available membrane area occupied by the protein.

The recognition moiety concentration may be expressed in terms of number per channel or nmols/mm$^2$. A range of from 1 to about $10^9$ molecules per channel, or from about $10^{-10}$ to about $10^{-1}$ nmols/mm$^2$ is feasible. A range of from about $10^2$ to about $5 \times 10^7$ per channel or about $10^{-8}$ to about $2 \times 10^{-3}$ nmols/mm$^2$ is preferred. Ranges are affected by stoichiometry of recognition moiety to gate material channels, and by the thickness of the switch layer.

Channel blocker concentration may range from about 1 to about 10 moles per mole of recognition moiety, preferably in the range of about 1 to about 2. The nature of the relationship between the channel, the blocker, and the recognition moiety will determine the most appropriate ratios.

The switch layer thickness may range from about $10^{-4}$ mm to about 0.2 mm. For practical purposes, a preferred thickness would lie between 0.001–0.1 mm. The thickness of the gate membrane may lie in the range of from about $3 \times 10^{-6}$ to about $10^{-4}$ mm, preferably about $5 \times 10^{-6}$ to about $2 \times 10^{-5}$ mm.

The D.C. component of the transmembrane voltages typically employed consistent with the invention range from 0 to about 20 V, preferably in a lower range of from about 0 to about $+/-0.1$ V, or in a higher range of from about 1 to about 3 V. The AC component, when desired for noise analysis, may range from about 0 to about 10 mV.

The detectable membrane current surge resulting from operation of the biochemical switch may range from about 10 pA to about 10 mA. With D.C. voltage in the lower preferred range, the current surge will preferably fall in the range of from about 10 to about 100 pA. In the higher preferred range of D.C. voltage, the detectable current surge will preferably fall within the range of about 0.01 to about 0.10 mA.

In the various embodiments of the invention, highly sensitive biosensors may be constructed. The sensitivity of a biosensor in accordance with the invention to target agents is much greater than a sensor relying directly on chemical or physical properties of the target agent, and may be as great as $10^{-13}$ nmols. In typical embodiments, the target agent may be detected at concentrations ranging from about $10^{-10}$ to about $10^{-4}$ nmols. The speed of the detection reaction may range from less than 1 second to over 6 hours, but is preferably within the range of about 5 seconds to about 15 minutes.

The embodiments of the invention are best understood from the examples, although the numerical ranges provided above can help understand how to obtain the benefits of the invention.

Examples of target agents whose detection by the sensor of the present invention would be particularly useful include: environmental pollutants, AIDS virus or antibodies or fragments thereof, botulinum toxin in foodstuffs, bacterial cell fragments or debris thereof particularly for infectious organisms, hepatitis viruses or fragments thereof, human antibodies to antibiotics for detection of allergic sensitivity, messenger proteins for immunosuppression, or enterotoxins for food poisoning detection. Without doubt, the present invention could be similarly designed to detect many other target biomolecules, far too numerous to mention specifically, as the needs dictate. Use of the present invention is anticipated in health care industries, medical and pharmaceutical laboratory operations, personal screening applications, quality control in food processing and distribution, gene product quality control in genetic biotechnology industries, among others.

Embodiments of the present invention are described in the examples.

EXAMPLE 1

To the cis- chamber of a Mueller-Rudin bilayer membrane apparatus (Urban, B. W., S. B. Hladky, and D. A. Haydon (1980) "Ion Movements in Gramicidin Pores An Example of Single File Transport," *Biochimica et Biophysica Acta* 602: 331–354, for example), gramicidin D was added to a total bulk concentration of 8 nM, and allowed to diffuse into a membrane of brain phosphatidylcholine and phosphatidylethanolamine lipids (Avanti, Birmingham, Ala.) in n-decane which had been applied by streaking across a 0.2 mm orifice in the apparatus.

Figure 2:
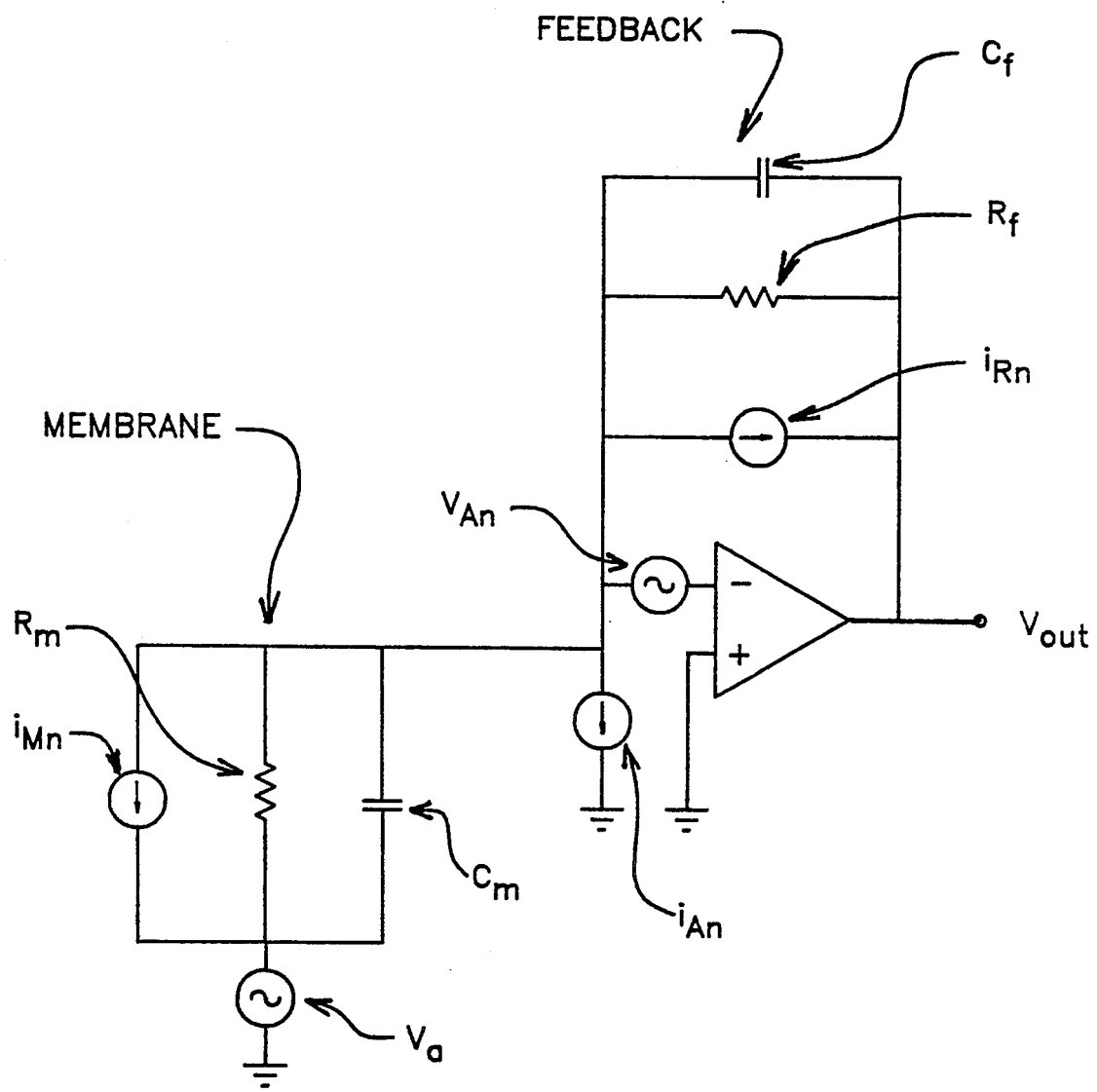
FIG. 2 shows an equivalent circuit diagram for the detection of ion currents across membranes in a Mueller-Rudin test system.

A Mueller-Rudin black film apparatus for membrane conductance measurements consists of two cells, one in which the contents could be stirred and exchanged, separated by an orifice across which a membrane is applied. Two Ag-AgCl electrodes are used, one in each cell. One electrode was connected to a low-impedance potentiometer, the other to the negative input of a high-impedance operational amplifier. An equivalent circuit diagram is shown in FIG. 2, for the black film and current-to-voltage amplifier. In it, noise originating from the membrane ($V_{Mn} = i_{Mn}R_m$), the feedback resistor ($V_{Rn} = [4kTR_f]^{\frac{1}{2}}$, where kT is the thermal energy and $\Delta f$ the frequency bandwidth), and the operational amplifier ($V_{An}$ = approx. 0.008 mV, and i = approx. 5 fA) affect the output voltage ($V_{out}$), according to the following formula:

$$V_{out} = - \\ V_a \frac{Z_f}{Z_m} + V_{Rn}\frac{Z_f}{R_f} + V_{Mn}\frac{Z_f}{R_m} + V_{An}\left(\frac{Z_f}{Z_m} + 1\right) + Z_f i_{An}$$

A 1–10 Gigaohm feedback resistor ($R_f$), the major noise source other than the membrane, contributes less than 0.1 pA current noise. The two aqueous compartments of the bilayer chamber are filled with identical electrolyte solution, a voltage applied across the membrane, and the resulting discrete current steps (typically 0.1–10 pA) measured.

Four discrete ion channels formed from the gramicidin dimers, each one conducting 0.95 pA at a transmembrane potential of $-60$ mV. Addition of aqueous DyCl$_3$ to a final concentration of 0.025 mM in both cis- and trans- chambers lowered the ion channel current to 0.85 pA. Further DyCl$_3$ addition to 0.050 mM dropped the ion channel current below 0.2 pA, thus effectively blocking the channels. Successive additions of bovine serum albumin (BSA) to the system with Dy-blocked channels resulted in gramicidin channel current levels of 0.3 pA at 0.0065 mM protein and 0.4 pA at 0.027 mM protein, respectively. Gramicidin channels remained substantially blocked, despite the fact that essentially all of the free Dy(III) ions had been sequestered by the protein. Control experiments in which free BSA was added to a level of 0.010 mM showed no effect on gramicidin channel current.

EXAMPLE 2

Dy(III)-bound bovine serum albumin was prepared by titrating a 1 mM solution of the protein in imidazole buffer with $DyCl_3$ to a final concentration of 5 mM. At the 5:1 mol ratio of lanthanide, the free Dy(III) concentration was less than 0.010 mM based on colorimetric analysis with murexide. Aliquots of the Dy(III)-protein complex were then added to the cis- chamber of the bilayer membrane apparatus described above in Example 1. Two discrete ion channels were apparent in the phospholipid membrane with gramicidin D from an initial addition of 2 nM, with conductance of 1.17 pA each at −65 mV. Addition of the Dy(III)-protein complex to a concentration of 0.035 mM reduced the gramicidin channel current to 0.15 pA. No free Dy(III) was detected in the system.

Channel blockage occurred rapidly, within seconds, and was essentially complete. A similar addition of the complex to 0.008 mM concentration resulted in an ion channel current of 0.62 pA, which represents approximately 50% inhibition.

The biochemical switch was thus turned on by a target agent. Subsequent addition of antibody against bovine serum albumin ("anti-BSA") elicited a resumption of gramicidin channel current, to a level of 0.97 pA at 0.0025 mM antibody, and 1.0–1.1 pA at 0.0035 mM antibody. Thus, an immunological reaction of a protein-conjugated gramicidin channel blocker effectively removes the blocking agent from the ion channels. This example demonstrates the functioning of a biochemical switch which is alternately turned off by a channel blocker then turned on by a target agent.

EXAMPLE 3

A hydrophobic mixture containing 51.5 mg of a diunsaturated aldehyde of the general formula $C_{17}H_{29}CHO$ (melting point, approximately 30° C.), 22 mg of the corresponding alcohol, $C_{17}H_{29}CH_2OH$, 12 mg of the corresponding carboxylic acid $C_{17}H_{29}COOH$, and 44 mg of n-decane, was dissolved into 0.2 mL n-hexane. This mixture solidifies as the hexane evaporates or disappears. When streaked over the pinhole in a Mueller-Rudin apparatus as described above in Example 1, a membrane formed with the conductance characteristics shown for the "Control" column in Table 1. Addition of gramicidin D to a bulk concentration of 10 nM in the cis- chamber, a quantity sufficient to maintain 3–5 ion channels in the membrane, increased the conductance as shown in the "Open" column in Table 1. Addition of a 1:1 Dy(III)-BSA complex, to a final bulk concentration of 0.020 mM in both the cis- and transchambers, resulted in a reduced conductance, as shown in the "Blocked" column of Table 1. Depending on membrane composition, ion currents with gramicidin channels can range from −0.5 to −1.2 pA at −100 mV. The Table 1 results are consistent with the presence of 1–3 gramicidin channels frozen in an open configuration in a solid membrane, subject to blockage by a lanthanide-protein conjugate.

TABLE 1

| Applied Voltage (mV) | Ion Current Across Membrane (pA) | | |
|---|---|---|---|
| | Control | Open State | Blocked State |
| 0 | 0 | 0 | 0 |
| −20 | −0.2 | −0.45 | −0.25 |
| −40 | −0.35 | −0.8 | −0.5 |
| −60 | −0.45 | −1.3 | −0.7 |
| −80 | −0.65 | −1.7 | −0.95 |
| −100 | −0.8 | −2.2 | −1.2 |

EXAMPLE 4

1.2 mg of a diunsaturated alcohol of the formula $C_{17}H_{31}CH_2OH$ plus 2.0 mg of the diunsaturated aldehyde $C_{17}H_{31}CHO$ (both "$C_{18}$" compounds, the same as those used in Example 3, above) was mixed in 0.4 mL of a $CHCl_3$ solution containing 1.8 mg phosphatidylserine ("PS", Avanti, Birmingham, Ala.) and 2.2 mg of phosphatidylethanolamine (PE) which, after solvent evaporation under $N_2$, was mixed into 0.12 mL of 1:1 n-hexane:n-decane. Omission of the $C_{18}$ carboxylic acid derivative of Example 3 was believed to improve both the stability of membranes toward polyvalent cations and the selectivity of Dy-protein conjugates as in Example 2 for gramicidin channels. Surface potential effects of negative charges which could interfere with Dy-protein conjugate interactions by presenting too many bonding sites might be eliminated by omission of the $C_{18}$ carboxylic acid component. Except for the solvent evaporation, all preparative and use steps were carried out aerobically, with $C_{18}$ aldehyde and phospholipid materials which were noticeably yellow from partial autoxidation ("lipid peroxidation," verified spectrophotometrically). The membrane was prepared as in Example 1.

Overvoltage transients of some 15–16 V across the membrane result from the act of turning off then turning on the main power to the Mueller-Rudin apparatus. With ordinary phospholipids such as those used in Examples 1 and 2, this procedure instantly explodes phospholipid bilayer membranes. Partially oxidized phospholipids conventionally give membranes which are even more fragile. With the present organic composition, overvoltage spikes across the membrane did not cause rupture, through at least seven "off-on" cycles of the power source. Despite the suboptimal materials and handling conditions, bilayer membranes with exceptional physical stability were obtained—far superior to conventional lipid bilayers.

EXAMPLE 5

In order to examine charge related effects on stability and electrical activity of plastic bilayer membranes, two thin film plastic derivatives were examined, as in Example 1. One material ("E") consisted of 0.01 mL of a 1N poly(2-vinylpyridine-co-styrene, from Aldrich, Milwaukee, Wis.) solution (with respect to pyridine-nitrogen) in toluene, mixed with 0.03 mL of an n-decane solution of partially oxidized 0.6 mg PS and 0.75 mg PE (as in Example 4). The second material consisted of the N-methylated polymer ("F") prepared by titrating polymer "E" with a 1N solution of $CH_3Cl$ in diethyl ether, and containing the same lipid composition as "E". The latter material "F" contained a large excess of surface cations, and was expected to exhibit significantly increased conductance in a membrane.

Figure 3A:
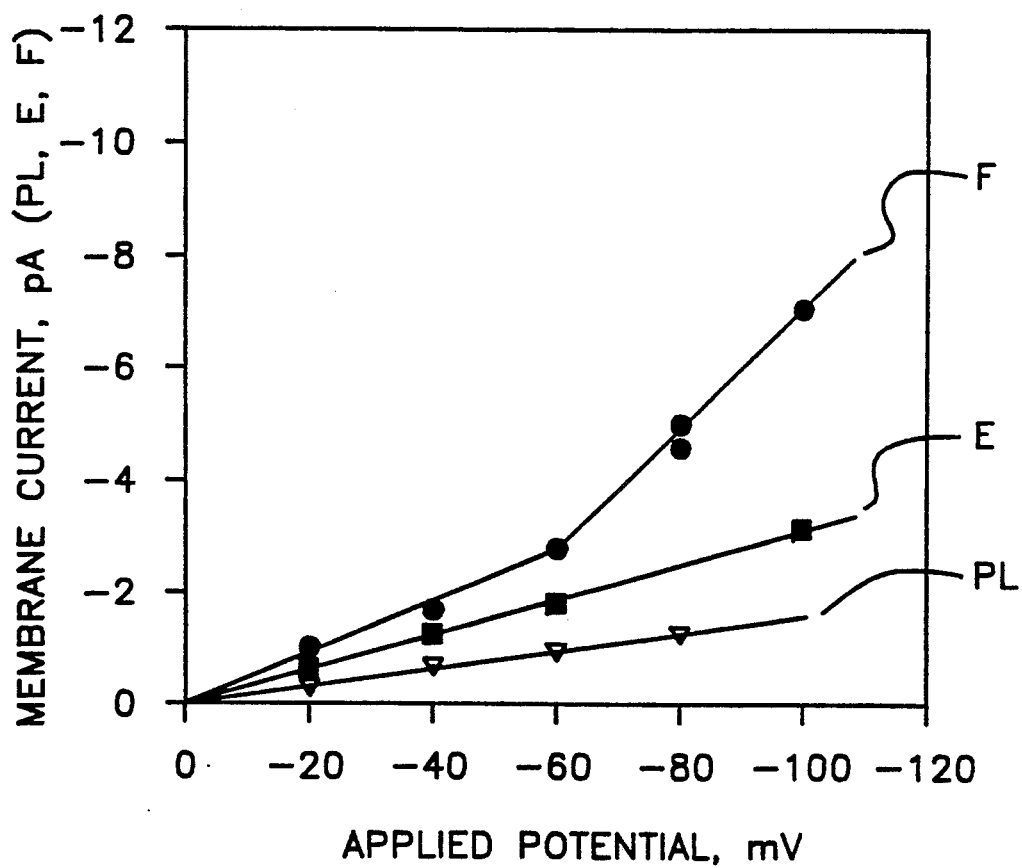
FIGS. 3A and 3B, hereinafter collectively referred to as FIG. 3 shows current-voltage curves for ion conduction in two thin film plastic membranes, compared to a conventional phospholipid bilayer membrane, to demonstrate the effect of surface electric charge on ion currents.
Figure 3B:
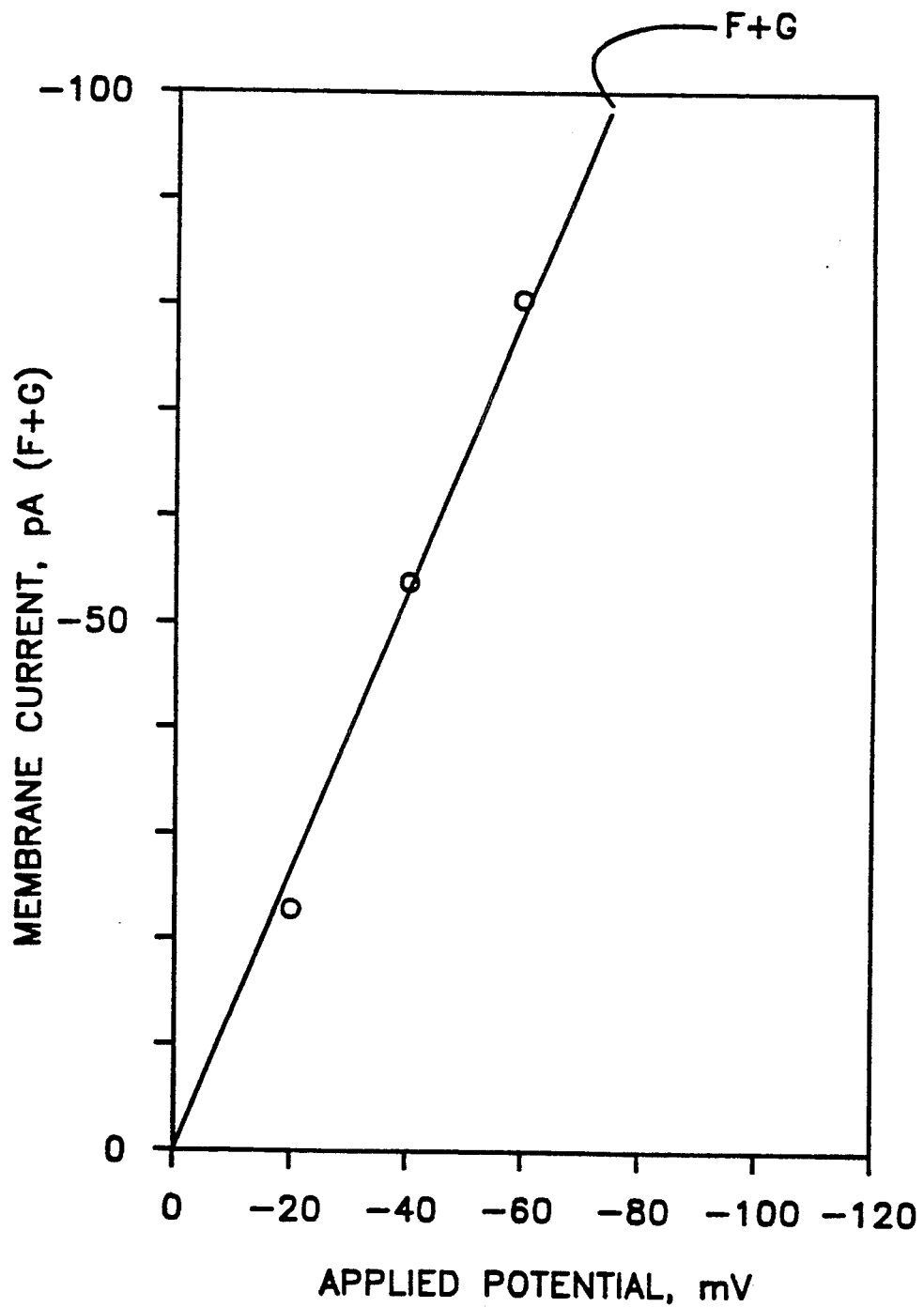

FIG. 3 shows steady-state current voltage curves for the two plastic membrane preparations "E" and "F", relative to that for a pure phospholipid bilayer membrane "PL", and a test membrane "F+G" in which 0-3 mM gramicidin D was added to material "F" immediately prior to preparation of the membrane. While the cationic N-methylated material ("F") was more conductive, its ability to carry a gramicidin-mediated ion current (Curve "F+G") was considerably less than that observed for an uncharged plastic membrane material (Compare the curve for "F+G" in FIG. 3 with the curve for "1" in FIG. 6, described below in Example 8). A positively charged membrane reduces sensitivity, presumably because gramicidin produces a cation channel, and the cations are repelled by the positive charge.

Membranes prepared with either material "E" or "E" ruptured after 4-6 rounds of "off-on" overvoltage spikes as in Example 4. This nonetheless represented an improvement over bilayer membranes prepared with conventional phospholipids as in Examples 1 and 2.

EXAMPLE 6

A hybrid lipid-plastic material was prepared by air drying under direct sunlight 0.27 mL of an aged $CHCl_3$ solution containing 1.2 mg PS and 1.5 mg PE. This procedure assists further lipid peroxidation in the material. After resuspension into 0.05 mL unfiltered n-decane, this material was admixed with 0.05 mL of a solution containing one part polylauryl methacrylate (20% in tetrahydrofuran, Aldrich, Milwaukee, Wis.) and two parts n-hexane. The mixture was then diluted further with 0.05 mL n-decane and 0.05 mL n-hexane, giving a final solids loading of 4.0 mg polylauryl methacrylate and 2.7 mg phospholipids. This mixture contained gramicidin D at endogenous contamination levels only (approximately $10^{-6}$-$10^{-5}$ mM). Test membranes were prepared from these solutions by capillary thinning across the pinhole of a Mueller-Rudin apparatus as in Examples 1 and 2.

Figure 4:
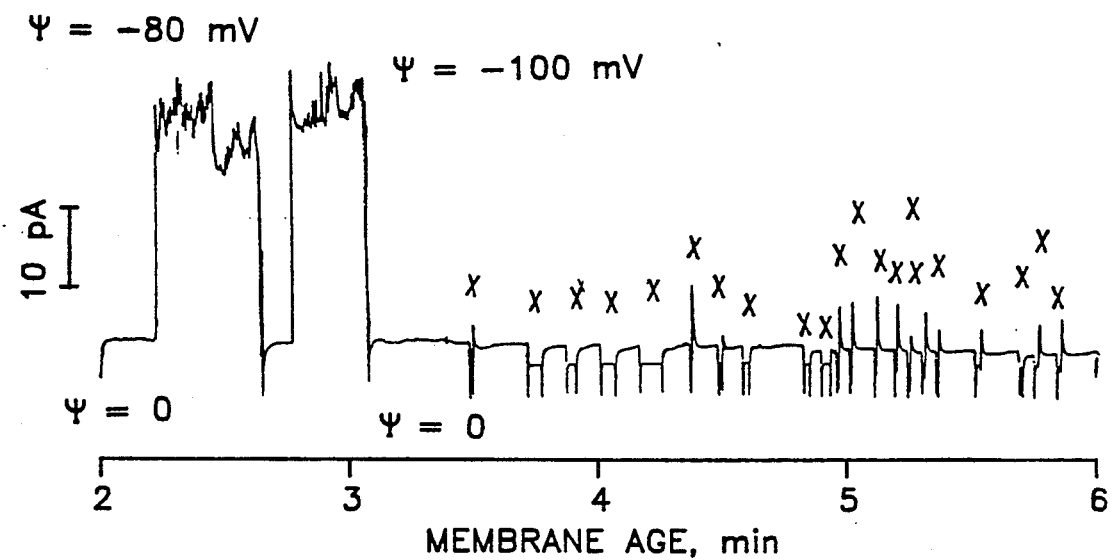
FIG. 4 shows a time history for a polylaurylmethacrylatelipid composite membrane with endogenous gramicidin ion channels, to demonstrate its durability toward physical and electrical voltage stresses.
Figure 4:
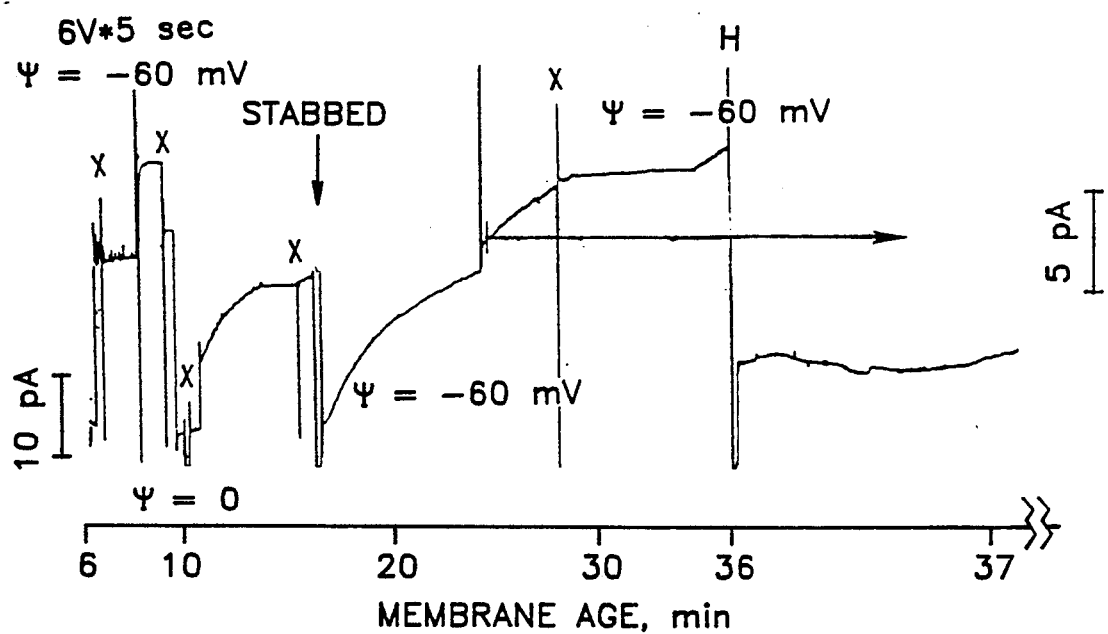
Figure 4:
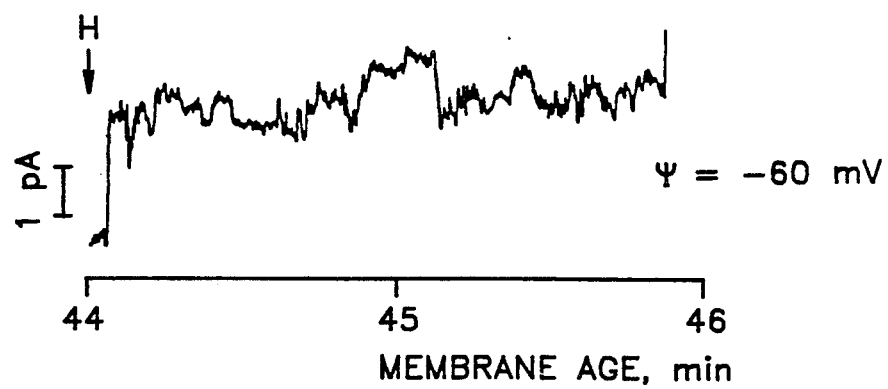

FIG. 4 shows the time history of one such membrane. Applied steady-state potentials across the membrane (identified by "$\Psi$" in FIG. 4) varied from 0-100 mV, except that where indicated by "6V*5sec," a 6-Volt battery was connected across the membrane for a 5 sec duration. Overvoltage spikes of 15-16 V generated by "off-on" transients (as in Example 4, above) are identified by "X" in FIG. 4. After 27 rounds of overvoltage spikes, plus physical stabbing with a straight pin ("STABBED" in FIG. 4), the membrane remained intact. Following irrigation of the membrane by n-hexane ("H" in FIG. 4) to re-fluidize the membrane material, performed by pipetting 0.002-0.005 mL of the liquid to within 0.1 mm of the membrane from the cis-chamber of the Mueller-Rudin apparatus, ion current transients resume in increased frequency, as shown in the third line of the Figure.

Electrical noise in the figure, particularly at steady-state potentials of $-60$ to $-100$ mV, is due primarily to the action of gramicidin D-dimer ion channels opening and closing as dimers associate and dissociate and is indicative of the plastic membrane in a highly fluid state. As the membrane freezes or solidifies, at times beyond 10 min in the figure, opening and closing events occur much less frequently, and the electrical noise level decreases. Re-fluidizing with n-hexane restores some of the noise transients. Autocorrelation analysis of the noise indicates electrical conductance states of 12 picoSiemens and 4-5 picoSiemens for the gramicidin D channels in this membrane composition. This demonstrates the ability of the circuitry of the invention to distinguish ion channel effects from unrelated disturbances in the membrane.

EXAMPLE 7

The membrane-forming material of Example 4 was pre-loaded with 0.00064 mM gramicidin D to a final concentration of $10^{-5}$ mM gramicidin D. Then, a membrane of this material was prepared by streaking it across the orifice of a Mueller-Rudin apparatus as in Examples 1 and 2. Subsequent capillary thinning resulted in a bilayer membrane with the conductance shown in curve "O" of FIG. 5.

Figure 5:
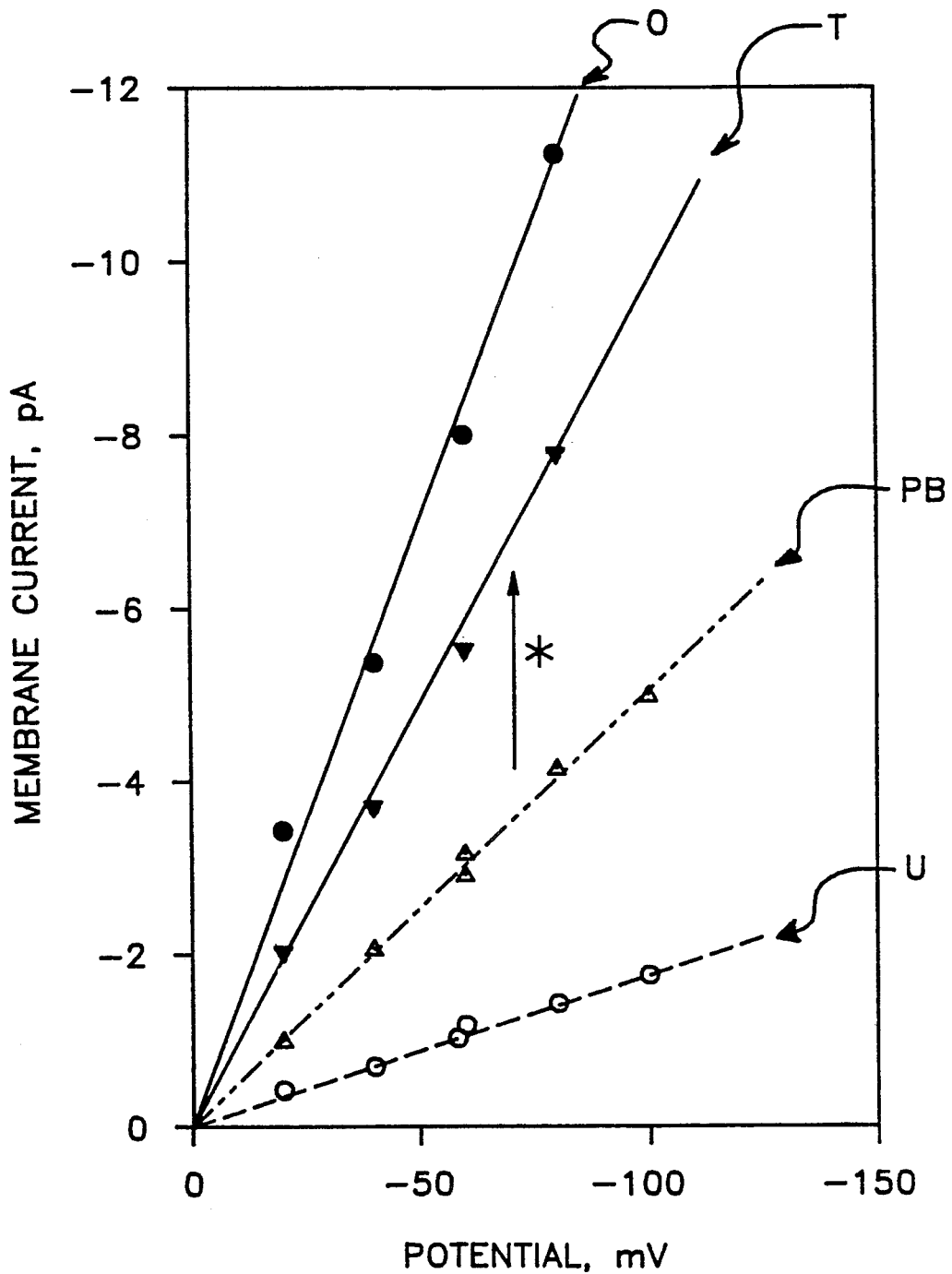
FIG. 5 shows the effects of protein-blocker conjugates and immunochemical triggering on ion currents in hardened membranes containing $C_{18}$ compound-lipid composites loaded moderately with gramicidin D ion channels.

FIG. 5 shows the steady-state time-weighted average current-voltage profiles for this membrane. The slope represents the electrical conductance (in pS) of the membrane, under each of the respective test conditions. A straight line slope indicates that Ohm's law is obeyed for the present system. Curve "O" represents the gramicidin-loaded membrane with a conductance of 150 pS. By comparison, a similar membrane without any gramicidin constituent contained therein ("U") gives a much smaller slope, corresponding to approximately 14 pS conductance.

Addition of 0.02 mM of a Dy-conjugated albumin, similar to that described Example 2, results in a conductance decrease to 46 pS. Thus, effective ion channel blocking by the lanthanide-protein conjugate is demonstrated, although the efficiency does not quite equal that for the unloaded membrane ("U") which had contained no gramicidin in its formulation.

Presumably, blocker concentration was below the saturation point. In a wheatstone bridge circuit, the background state is nulled, and so using concentrations below saturation is possible, allowing greater tolerance. Subsequent addition of 0.01 mM antibody against the Dy-conjugated protein of curve "O" increases the electrical conductance of the membrane to the 100 pS state shown by Curve "T" of FIG. 5. These results confirm the value of an immunochemical trigger mechanism for chemical or biological agent detection in a hardened artificial membrane, and demonstrate the function of the biochemical switch.

In Example 8, use of a plastic lipid composite for the membrane of the sensor is described, and the triggered electrical activity in response to an immunological reaction is demonstrated. Examples 9 and 10 extend these descriptions to the simple direct current measurement in a simple metal electrode chip configuration. Example 11 describes the incorporation and use of a physiological ion channel protein, specifically calcium channels from mouse heart sarcoplasmic reticulum, in a plastic lipid composite membrane.

EXAMPLE 8

A hybrid lipid-plastic material similar to that in Example 6 was prepared by air drying a $CHCl_3$ solution containing 1.2 mg PS and 1.5 mg PE. After resuspension into 0.05 mL unfiltered n-decane, this material was admixed with 0.05 mL of a solution containing one part polylauryl methacrylate (20% in tetrahydrofuran) and two parts n-hexane. The mixture was then diluted further with 0.05 mL n-decane and 0.05 mL n-hexane, giving a final solids loading of 4.0 mg polylauryl methacrylate and 2.7 mg phospholipids. To one volume of this mixture was then added an equal volume of 0.6 mM gramicidin D in ethanol, giving 0.2 mg in the mixture. A membrane was streaked across the orifice of a Mueller-Rudin apparatus as in Example 1, and its electrical conductance measured from the slopes of the current-voltage curves of FIG. 6.

Figure 6:
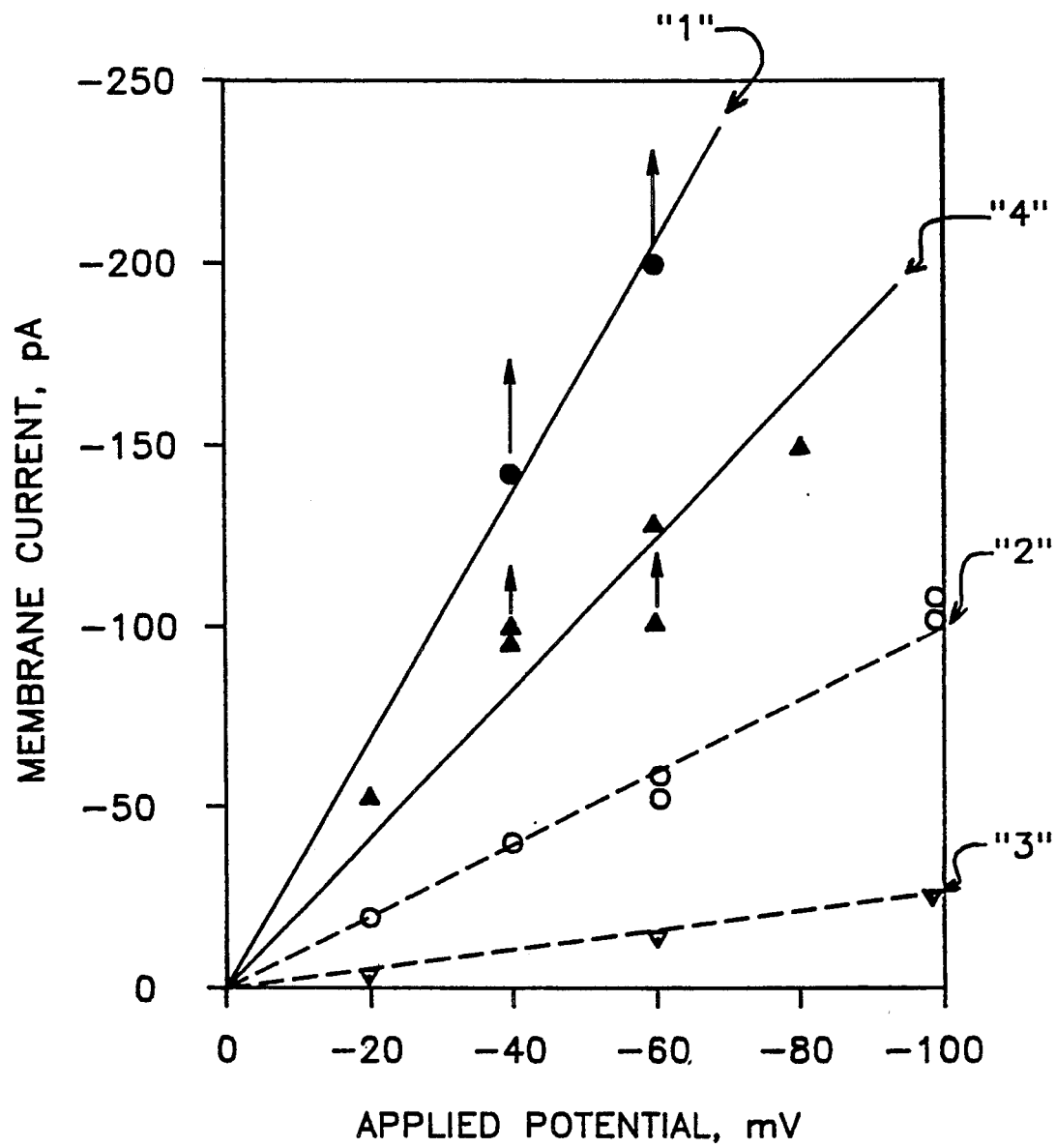
FIG. 6 shows the effects of protein-blocker conjugates and immunochemical triggering in hardened membranes containing acrylic polymer-lipid composites loaded heavily with gramicidin D ion channels.
Figure 7:
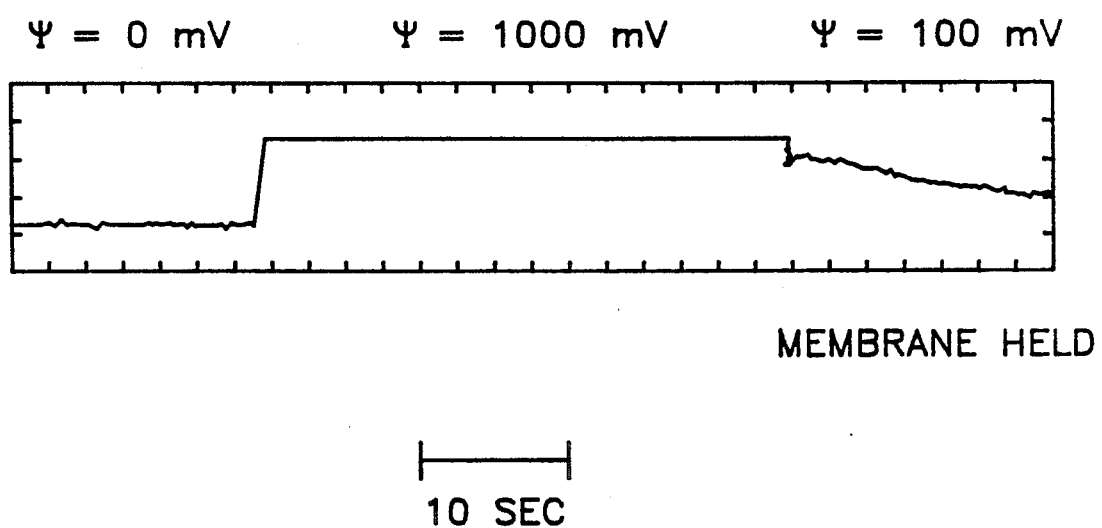
FIG. 7 shows a time course for an acrylic polymer-lipid composite membrane containing calcium channel proteins, to demonstrate the durability of this system to voltage stresses.
Figure 8:
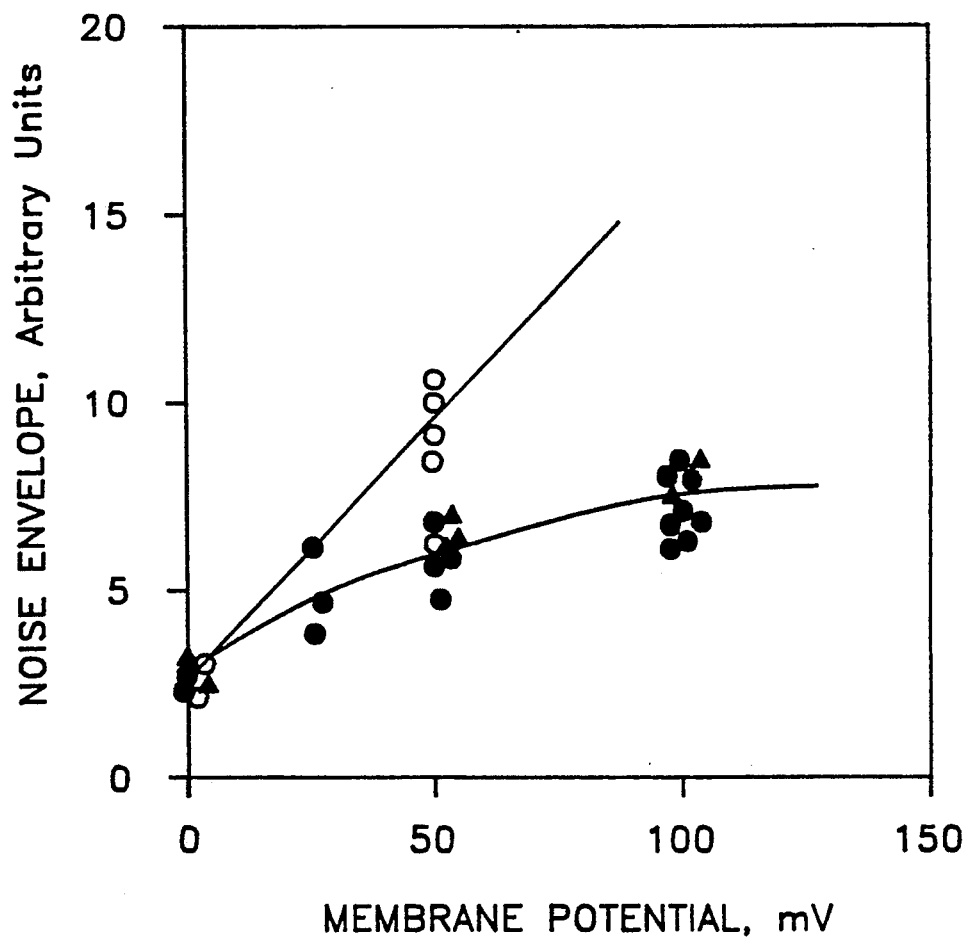
FIG. 8 shows the effects of activators and blockers on voltage-dependent membrane noise due to calcium channel proteins in the FIG. 7 membrane, to demonstrate retention of physiological activity, regulation and control under conditions applicable in an artificial sensor system.

In FIG. 6, Curve "1" represents a lower limit of the conductance of the initial membrane, at least 3,300 pS as shown by the arrows pointing upward in the figure. Addition of a 10:1 stoichiometric complex of gadolinium-bovine serum albumin ("Gd-albumin"), to a final concentration of 0.02 mM in both the cis- and trans-chambers of the apparatus, lowers the conductance within the first 2 min to a value of 950 pS (curve "2"), and subsequently to a lower value of 220 pS after 7 min, which is less than 1/15 of the original value. At this point, ion channels in the membrane have been effectively blocked. A subsequent addition of antibody against bovine serum albumin ("anti-BSA") to a final concentration of 0.010–0.014 mM in both the cis- and trans- chambers restored the membrane conductance to a value of 2,100 pS, or some ⅔ of the original electrical current. The biochemical switch was closed and opened, yielding a measurable current surge.

The test membrane of this example held an estimated time-weighted average of 400–500 gramicidin D channels in their open state. Sufficient gramicidin D was present stoichiometrically to support some $10^3$–$10^4$ times this number of ion channels. On the other hand, only a small fraction of the available plastic material volume actually accounted for the test membrane area. From this Example, triggered current densities on the order of at least 6–7 mA/m² at −0.06 V stimulus potential have been shown. Because this membrane can tolerate stimulus potentials as high as 6 V (Example 6), a system capability of 600–700 mA/m² is shown to be feasible.

EXAMPLE 9

Circular steel alloy metal chips available as junction box knockouts, approximately 100–200 mm² in available surface area, serving as electrodes, were wired to simple resistive circuitry driven by a 1.5 V battery through a 10K–47K ohm resistor series and an ammeter. Gate membranes were applied in the gap between the ammeter and the electrodes. Under these conditions, aqueous films supported a current load on the order of 0.10 mA–0.6 mA, which was easily distinguishable from the <<0.01 mA currents through canola oil films. For comparison to the Example 8 results, a current surge of 250 pS translates to an effective current density on the order of 0.10 mA at the supply voltages in this Example, provided: (1) the necessary bilayer membrane can be spread over a 100–200 mm² area; and (2) the bilayer membrane employed can withstand supply potentials of 1.5–9.0 V.

Metal test chips were coated with 0.018–0.020 mL of a diluted or undiluted latex emulsion of a carboxylated acrylamide polymer marketed under the trade name "RHOPLEX N580" which was spread gravitationally over the entire area of the chip. Conductance due to a 1.5 V direct current source was measured amperometrically with an ovoid Ag-solder electrode (Area=approx. 15–20 mm²) and resistive breadboard circuitry. In the absence of an effective electrical barrier (e.g., membrane), a stable current of >0.100 mA was obtained. The emulsion was allowed to dry in air into a surface film which could then be analyzed in the dry state, overlaid with an aqueous salt solution or gel, and analyzed again wet. In some experiments, a small volume of an ethanolic solution of gramicidin S was also added to the system. Table 2 shows the results.

TABLE 2

Thin Film Deposition and Membrane Conductance

| Run # | Plastic Latex Concentration | Est. Film Thickness | Elec. Conductance (mA) Dry Chip | Elec. Conductance (mA) +Water Overlay |
|---|---|---|---|---|
| Blank | None | None | >0.10 | >0.10 |
| A | 56.0% (w/w) | 100000 nm | 0.005–0.008 | n.d. |
| B | 1.0% (w/w) | 5000 nm | <0.004 | n.d. |
| C | 0.01% (w/w) (50% EtOH medium) | 18 nm | 0.05 ± 0.05 | 0.010 |
| C' | Same, +0.01 mL 10 mM gram. S | 900 nm | 0.000 | 0.036 |
| D | 0.01% (w/w) (THF medium) | 18 nm | 0.080 ± 0.04 | n.d. |
| E | 0.01% (w/w) (<25% EtOH med.) | 18 nm | 0.000 | 0.000 |
| F | 0.01% (w/w) (<25% EtOH med.) +0.0018 mL of 10 mM gram. S | 100 nm | 0.000 | 0.026 |
| G | 0.01% (w/w) (~25% EtOH med.) | 18 nm | 0.025 ± 0.025 | 0.000 |
| H | 0.01% (w/w) (~25% EtOH med.) +0.5 mM gram. S | 50 nm | 0.050 ± 0.050 | 0.060 |

In Run "A" (Table 2), 0.018 mL of a 56% (w/w) aqueous emulsion of the above latex was spread onto a 100 mm² metal chip. Wetting proceeded readily, and an apparently uniform film with an estimated thickness on the order of 0.1 mm resulted. It was electrically nonconductive.

In Run B, wetting proceeded less readily than in Run A, largely because dilution of the plastic latex also resulted in dilution of any surface-active additives which might have been present in the original latex. Nevertheless, a good evenly spread membrane was formed, without obvious signs of island formation.

Run C represented a further dilution of the latex, to a concentration sufficient to form a film on the order of 18 nm thickness. Surface wetting of the metal chip required addition of ethanol (EtOH) to a final concentration of approximately <50%. However, visual inspection of the dried film did not reveal signs of island formation. At this loading, the film thickness was within a factor of 3 times the thickness of a bilayer lipid membrane (conventionally reported to be 5–6 nm). Minor aggregation without discrete islands, and thus without zones of direct electrical contact with the metal surface, might not be visually detected at these dimensions. Separate experimental tests, in which higher ethanol concentrations were used, revealed substantial island formation.

In Run C', a solution of gramicidin S was plied directly over the membrane of Run C by careful surface application in a manner familiar to one of skill in the art. After drying, the conductance of the film was measured in the dry state, then again after applying an aqueous KCl overlay. The substantial current increase observed in the wet state, but not dry, strongly suggests a gramicidin-mediated conduction mechanism in the test chip.

Run D attempted to produce essentially the same membrane structure as Run C. Only the solvent vehicle (in this case, tetrahydrofuran, "THF," instead of an aqueous ethanol mixture) differed. Island formation was visually evident, and the electrical conductance measurements pointed to the same conclusion. THF is a lipophilic but chaotropic liquid, which was originally considered a good candidate to reversibly break down the structure of the latex emulsion particles into a homogeneous plastic solution. In fact, THF did not effectively dissolve the emulsion in this example. Other solvents which also present difficulties with effective dissolving of the emulsion include $CH_2Cl_2$ and methanolacetone.

Run E conditions were similar to Run C, but employing less EtOH in the surface preparation and spreading step. This run is shown in Table 1, as a control condition for Run F. A good membrane was formed on the chip surface, which was non-conductive under both dry conditions and wet (i.e., with an aqueous KCl overlay).

In Run F, gramicidin S was added to the latex emulsion on the test chip, which was then air dried and evaluated. In the dry state, no measurable conductance was observed. Hence, an intact membrane had formed. After applying an aqueous KCl solution overlay, however, the current increased to 0.026 mA, consistent with a gramicidin S-mediated conduction mechanism.

Runs G and H were similar to Runs E and F respectively, except that gramicidin S in Run H was added to the stock latex emulsion prior to application to the test chip. 0.5 mL of 10 mM Gramicidin S in ethanol was added to 10 mL of the stock 0.01% latex emulsion. 0.018 mL of this emulsion was then plied to the test chip, and sufficient ethanol added (final concentration of approximately 25%) to assist wetting and spreading of the thin film. In these test runs, surface preparation and material spreading were becoming noticeably more difficult, with signs of island formation beginning to appear. Electrical current readings in the dry state for both runs had become less stable. However, wet conductance measurements remained stable, with a substantial increase still observed due to gramicidin S (Run H).

These results demonstrate electrical conductance due to gramicidin S activity on a metal electrode chip, measurable by conventional miniature electronics.

EXAMPLE 10

Four metal chips were coated with 0.018 mL of a 0.01% aqueous latex emulsion of a carboxylated acrylamide polymer marketed under the trade name "RHOPLEX N580" as in Example 9, with 0.0001 mM gramicidin D present in the emulsion for two of the chips (B+D) and absent from the other two (A and C), and air dried. Electric current measurements with a 1.5 V battery as in Example 9 were then performed dry, then the chips overlaid either with an aqueous 10 mM KCl solution (A and B) or a 1 mM solution of a 5:1 gadolinium-bovine serum albumin (GdS-BSA) complex (C and D). Table 3 shows the wet and dry ion currents.

TABLE 3

| Test Chip | Est. Film Thickness | Gramicidin D Content | Current: Dry (mA) | Overlay Material | Current Wet (mA) |
|---|---|---|---|---|---|
| A | 18 nm | 0.0 mM | 0.02 ± 0.02 | KCl—$H_2O$ | .02-.03 |
| B | 18 nm | 0.0001 mM | 0.01 ± 0.01 | KCl—$H_2O$ | .056 |
| C | 18 nm | 0.0 mM | 0.02 ± 0.02 | $Gd_5$—BSA | .074 |
| D | 18 nm | 0.0001 mM | 0.00 ± 0.01 | $Gd_5$—BSA | .030 |

The increased wet current in chip B relative to chip A demonstrates the effect of gramicidin D ion channel activity. The wet current difference between test chips B and D indicate gramicidin channel blocking action of the Gd-BSA conjugate. In this example, the magnitude of the effect appeared to be masked somewhat by an unexplained influence of the Gd-BSA conjugate, which increases the current in the absence of gramicidin channels, as shown by comparing chips A and C.

EXAMPLE 11

A solution containing 1 mg of polylauryl methacrylate plus 0.60 mg PS and 0.75 mg PE prepared as in Example 8 in 0.025 mL of n-hexane/toluene (4:1 v/v) was mixed with 0.02 mL of an aqueous buffer suspension of sarcoplasmic reticulum vesicles isolated from mouse cardiac muscle (Philadelphia Biomedical Research Institute, King of Prussia, Pa.). A milky emulsion resulted. This material was plied across a 1 mm diameter hole of a Mueller-Rudin cup containing in both the cis- and trans- chambers a solution of 0.25 M KCl plus 0.08 M sodium phosphate-bicarbonate buffer (pH=7.4). A stable membrane resulted, despite the fact that the material applied was a heterogeneous aqueous suspension including cell fragments.

FIG. 7 shows a time course for the membrane, including noise measurements pertaining to the Mueller-Rudin apparatus (Example 1) and to ion channel activity due to the sarcoplasmic reticulum calcium channels embedded in the membrane. The noise envelope at the left-hand region of FIG. 7 (transmembrane potential "Ψ"=0) is dominated by the electronics. In the intermediate region, in which the transmembrane potential was equal to 1 V, the membrane current was off scale, exceeding the capacity of the detection electronics to measure. At the right-hand region of FIG. 7, the transmembrane potential was lowered to 100 mV, and a membrane current noise pattern indicative of ion channel activity was evident. This time course demonstrated that the membrane, over a 1 mm diameter orifice, had withstood a 1 V stress for some 40 sec without rupture or breakdown. It is conventionally known that phospholipid membranes immediately explode under such a stress.

The 95% width of membrane current noise at voltage, which is related to ion channel opening and closing events by $2\sqrt{n}$, where n=the time-weighted average number of open ion channels, was determined as a function of applied transmembrane voltage.

The FIG. 8 membrane contained an undetermined number of sarcoplasmic reticulum calcium channels. The abscissa scale of FIG. 8 represents the applied transmembrane voltage. The ordinate scale corresponds to the noise envelope under the stated conditions. (Solid circles), *Sarcoplasmic reticulum* only, with no activators nor inhibitors present. (Open circles), Same membrane, to which 5 mM magnesium-ATP, an activator of the ion channels, had been subsequently added to the cis- chamber. (Solid triangles), Same membrane as "o" but subsequent to a trans- addition of 0.02 mM ruthenium red, a potent calcium channel blocker. The activator-dependent increase in current noise, followed by a corresponding reversal in the presence of a blocker, indicates that both the physiological activity and regulatory properties of sarcoplasmic reticulum calcium channels are retained in artificial plastic membranes. The membranes can, furthermore, function at potentials on the order of volts.

EXAMPLE 12

A solution containing 1 mg of polylaryl methacrylate plus 0.60 mg PS and 0.75 mg PE prepared as in Example 8 in 0.025 mL of dimethylsulfoxide/toluene (4:1 v/v) was mixed with 0.02 mL of an aqueous buffer suspension of sarcoplasmic reticulum vesicles isolated from mouse cardiac muscle (Philadelphia Biomedical Research Institute, King of Prussia, Pa.). A visually homogeneous solution/suspension resulted. This material was plied across a 1 mm diameter hole of a Mueller-Rudin cup containing in both the cis- and trans- chambers a solution of 0.25 M KCl plus 0.08 M sodium phosphatebicarbonate buffer (pH=7.4). A phase separation resulted, in which a stable membrane formed across the 1 mm orifice. Parallel control preparations, in which polylaurylmethacrylate was omitted from the medium, failed to give the necessary phase separation into a membrane. The 95% width of membrane current noise, which is related to ion channel opening and closing events by $2\sqrt{n}$, where n=the time-weighted average number of open ion channels, was determined as a function of applied transmembrane voltage.

Figure 9:
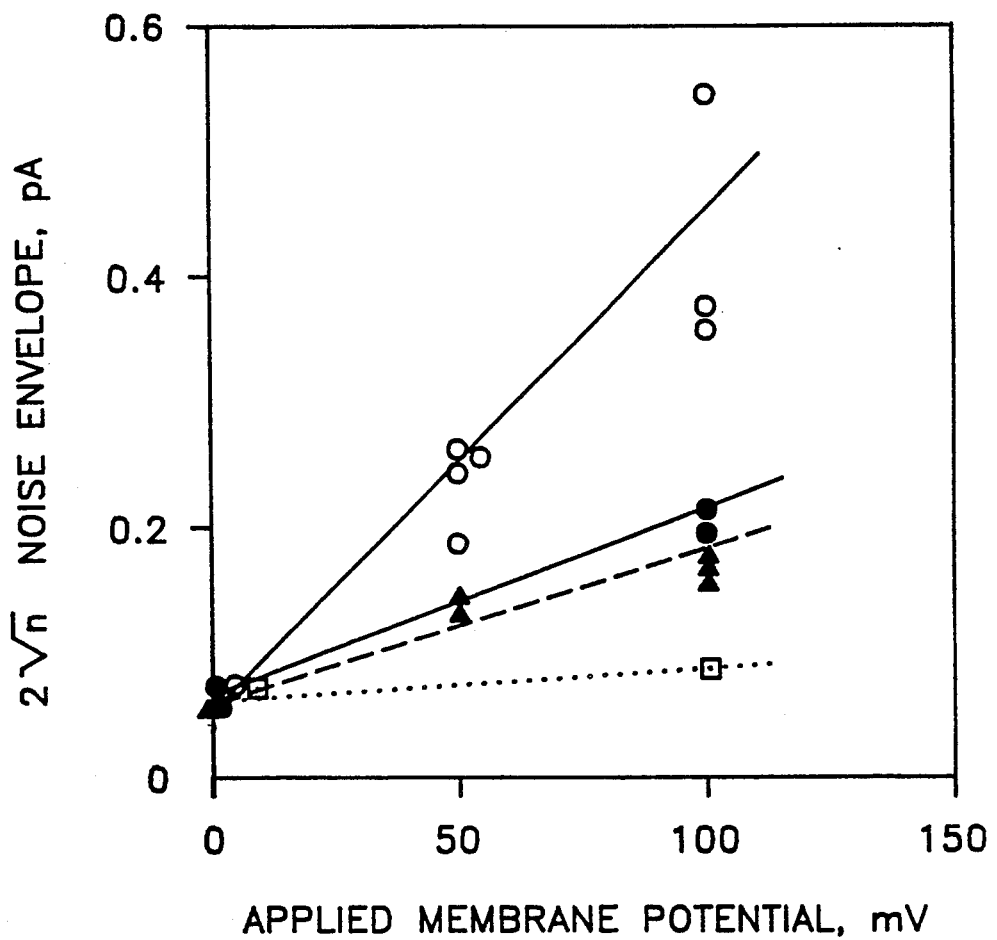
FIG. 9 shows the effects of activators and blockers on voltage-dependent membrane noise due to calcium channel proteins in an acrylic polymer-lipid membrane prepared by means of a dimethylsulfoxide-mediated phase separation, to further demonstrate retention of physiological activity, regulation and control under conditions applicable in an artificial sensor system.

The abscissa scale of FIG. 9 represents the applied transmembrane voltage. The ordinate scale corresponds to the noise envelope under the stated conditions. (Solid circles), *Sarcoplasmic reticulum* only, initial conditions. No activators nor inhibitors were present. (Open circles), Same membrane, but following addition of 20 mM $CaCl_2$ to the cis- chamber, activating the sarcoplasmic reticulum ion channels (in much the same fashion as Mg-ATP). (Solid triangles), Same membrane as "o" but following a subsequent addition of 0.02 mM ruthenium red, a $Ca^{2+}$ channel-blocker, to the trans- chamber. (Open squares), Control membrane prepared from the same materials, but in which sarcoplasmic reticulum vesicles were absent from the preparation medium. As in the previous example, both the activity and the regulatory properties of sarcoplasmic reticulum calcium channel protein are retained in artificial plastic membranes.

EXAMPLE 13

A solution of polylaurylmethacrylate and phospholipids, as in Example 8 above, was plied into membranes across the orifice of a Mueller-Rudin apparatus, as in FIG. 1 with orifice diameters of 0.2 mm, 1.0 mm, and 5 mm. Aqueous salt solutions of varying composition were present in both the cis- and trans- chambers, separated by the membrane. The longevities of the membranes without voltage and with applied voltage of 0.1 V and 1 V were observed.

Membrane longevity increased as the orifice diameter decreased and as the applied voltage decreased. A 5 mm orifice membrane lasts about 5–20 seconds without applied voltage, whereas a 0.2 mm membrane has a longevity running into days at an applied voltage of 0.1 V.

At an orifice diameter of 5 mm, membrane stability was limited to lifetimes on the order of 5–20 sec (n=25 determinations), which is sufficiently long to permit penetration of a 1–2 mm diameter electrode device through the membrane, and thereby applying the membrane to the surface of the electrode.

Thus, the biosensor can be manufactured by forming a membrane and passing an electrode through a solution of the biochemical switch medium to touch the gate membrane. The membrane is thus applied to the electrode and the biochemical switch layer is applied on top of the gate membrane as the electrode is withdrawn.

It is contemplated that a standard indicator module (the gate membrane with measuring device) can be produced separately and any desired biochemical switch layer can be either formed on or applied to the indicator module to complete production of the biosensor.

EXAMPLE 14

Four metal chips as in Example 10 are coated with 0.018–0.020 mL of a 0.01% aqueous latex emulsion of a carboxylated acrylamide polymer marketed under the trade name "RHOPLEX N580" as in Example 9, with 0.1 mM gramicidin D present in the emulsion for two of the chips and absent from the other two, and air dried. Estimated film thickness is approximately 18 nm. Electric current measurements are then performed dry, then the chips overlaid either with an aqueous salt solution or a 0.02 mM solution of a 1:1 gadolinium-bovine serum albumen (Gd-BSA) complex. This lower concentration of blocker reduces the masking effect noted in Example 10.

Table 5 shows the wet and dry ion currents. Subsequently, to the test chips is plied a solution containing approximately 0.014 mM antibody directed against bovine serum albumen (anti-BSA) as described in Example 8 above. The resulting changes in ion currents are shown in Table 5.

TABLE 5

| Test Chip | Gramicidin D Content | Current: Dry (mA) | Overlay Material | Current Wet(mA) | Current +Anti-BSA |
|---|---|---|---|---|---|
| A | 0.0 mM | 0.01 ± 0.01 | KCl—$H_2O$ | 0.010 | 0.010 |
| B | 0.1 mM | 0.02 ± 0.02 | KCl—$H_2O$ | 0.080 | 0.080 |
| C | 0.0 mM | 0.01 ± 0.01 | $Gd_5$—BSA | 0.010 | 0.010 |
| D | 0.1 mM | 0.02 ± 0.02 | $Gd_5$—BSA | 0.010 | 0.080 |

The wet current difference between test chips B and D indicates the efficiency of gramicidin channel blocking action of the Gd-BSA conjugate. The resurgence of ion current in test chip D following administration of antibody against bovine serum albumen (anti-BSA) demonstrates effective triggering in the present invention in response to the recognition reaction of the recognition biomolecule in the bioresponse simulator.

At this point, the test chips are rinsed gently with an exhaustive volume of 10–100 mM KCl to remove the overlay solutions. Electrical conductances return to the levels indicated by the "Wet" column for chip A (if gramicidin D is absent from the membrane) or chip B (if gramicidin is present in the membrane), regardless of history (including that for chip D). The sensor of the present invention is regenerated by repeating the gel overlay application procedure described above for chip D. The conductance of chip D then falls to the level shown in the "Wet" column for chip D in Table 5.

EXAMPLE 15

Four metal electrode chips are coated with a thin surface film of an acrylic polymer latex of the composition marketed under the trade name "RHOPLEX N580" as in Examples 9 and 10, to an estimated average thickness on the order of 6–18 nm. For the control chips ("A" and "C" of the following Table), gramicidin D is omitted from the latex. For chips of the present invention ("B" and "D" of the following Table), gramicidin D is added to the stock latex emulsion to a final concentration of 0.1 mM per 1% (w:w) solids, and the resulting emulsion diluted with 10–100 mM KCl to a final emulsion concentration of 0.01% (w:w) solids. After the film is plied to the electrode surface, it is air dried and tested for electrical conductance ("Dry" column of the following Table). A gel overlay containing approximately 2 mg/mL gelatin in 10–100 mM KCl as a stabilizer for the biochemical switch layer is plied to chips "A" and "B," representing controls which lack the recognition biomolecule (i.e., the protein-blocker conjugate or the like). A gel overlay of the same composition plus 0.01 mM immunoglobulin-gadolinium complex (Gd-IgG, at approximately 1:1 mole ratio) is plied to chips "C" and "D," in which the recognition biomolecule is present. Electrical conductance is then measured ("Wet" column of the following Table). Chip "D" under this condition represents the present invention in its poised state.

Application of an immunuglobulin gadolinium complex, prepared as described above, to the test chip D gives rise to the present invention in its poised state. The other test chips serve as controls in this Example. Subsequent addition of antigen to which the present IgG is directed, at levels approximately equal to a 1:1 titer (determined immunochemically by methods conventionally known in the art) initiates a reaction with the Gd-IgG in the bioresponse simulator in chip D. Table 6 shows the results.

TABLE 6

| Test Chip | Gramicidin D Content | Current: Dry (mA) | Overlay Material | Current Wet(mA) | +IgG Antigen |
|---|---|---|---|---|---|
| A | 0.0 mM | 0.01 ± 0.01 | KCl—H$_2$O | 0.010 | 0.010 |
| B | 0.1 mM | 0.02 ± 0.02 | KCl—H$_2$O | 0.080 | 0.080 |
| C | 0.0 mM | 0.01 ± 0.01 | Gd$_1$—IgG | 0.010 | 0.010 |
| D | 0.1 mM | 0.02 ± 0.02 | Gd$_1$—IgG | 0.010 | 0.080 |

The wet current difference between test chips B and D indicates the efficiency of gramicidin channel blocking action of the Gd-IgG conjugate. The resurgence of ion current in test chip D following administration of antigen demonstrates effective triggering in the present invention in response to the recognition reaction of the recognition biomolecule in the bioresponse simulator.

At this point, the test chips are rinsed gently with an exhaustive volume of 10–100 mM KCl to remove the overlay solutions. Electrical conductances return to the levels indicated by the "Wet" column for chip A (if gramicidin D is absent from the membrane) or chip B (if gramicidin is present in the membrane), regardless of history (including that for chip D). The sensor of the present invention is regenerated by repeating the gel overlay application procedure described above for chip D. The conductance of chip D then falls to the level shown in the "Wet" column for chip D in Table 6.

What is claimed is:

1. An electrochemical biosensor capable of signalling the presence of a target agent, comprising
   a. a biochemical switch comprising a hydrophilic film layer containing a recognition biomolecule, the recognition biomolecule having an ion channel blocker and a recognition moiety capable of specifically binding with a target agent,
   b. a hydrophobic gate membrane comprised of membrane material and ion channel gate material, in contact with the biochemical switch, and
   c. a measuring device comprising a conductive measuring electrode in contact with the gate membrane, and means for measuring a current surge between the biochemical switch and the measuring electrode in response to exposure to a target agent.

2. The biosensor of claim 1 wherein the recognition moiety is selected from the group consisting of an antibody to an antigen target agent, hapten to an antibody target agent, and antigen to an antibody target agent.

3. The biosensor of claim 1 wherein the ion channel blocker is a polyvalent cation.

4. The biosensor of claim 1 wherein the ion channel blocker is ruthenium red.

5. The biosensor of claim 1 wherein the channel blocker is a guanidinium compound and the ion channel is a sodium channel.

6. The biosensor of claim 1 wherein the ion channel blocker is a trivalent lanthanide.

7. The biosensor of claim 6 wherein the lanthanide is selected from the group consisting of dysprosium and gadolinium.

8. The biosensor of claim 1 wherein the recognition moiety is a protein selected from the group consisting of albumin and immunoglobulin.

9. The biosensor of claim 1 wherein the gate membrane is a plastic.

10. The biosensor of claim 1 wherein the gate membrane is a mixture of plastic and lipid.

11. The biosensor of claim 1 wherein the gate membrane comprises a solid layer of a mixture of alcohol, carboxylic acid and aldehyde with about 17 carbon atoms.

12. The biosensor of claim 1 wherein the gate membrane material comprises an acrylic polymer.

13. The biosensor of claim 1 wherein the gate membrane material is selected from the group consisting of polylaurylmethacrylate, carboxylated polyacrylamide, and styrene polyvinylpyridine copolymer.

14. The biosensor of claim 1 wherein the gate membrane material comprises a phospholipid or fatty acid derivative.

15. The biosensor of claim 1 wherein the gate material is selected from the group consisting of channel-forming antibiotics, physiological calcium channels, acetylcholine receptor channels, and physiological sodium channels.

16. The biosensor of claim 1 wherein the gate material is comprised of a gramicidin antibiotic ion channel.

17. The biosensor of claim 1 wherein the measuring device comprises a wheatstone bridge circuit.

18. The biosensor of claim 1 wherein the biochemical switch includes gelatin, the recognition biomolecule is an immunoglobulin-lanthanide conjugate, the gate membrane is a carboxylated acrylic polymer latex with gramicidin ion channels, and the measuring device is a resistance circuit capable of measuring a current surge when the biosensor is exposed to antigen.

19. The biosensor of claim 1 wherein the indicator means is an audible alarm.

20. The biosensor of claim 1 wherein the indicator means is a visible display.

21. The biosensor of claim 1 wherein the measuring device in contact with the gate membrane is constructed so as to be able to be regenerated and used with a variety of biochemical switches.

22. A method of using a biosensor, the method comprising:

providing a biochemical switch having a hydrophilic film layer containing a recognition biomolecule, the recognition biomolecule having an ion channel blocker and a recognition moiety capable of specifically binding with a target agent, a hydrophobic gate membrane containing ion channels in contact with the biochemical switch, and a measuring device, said measuring device comprising a conductive measuring electrode in contact with the gate membrane, and means for measuring a current surge between the biochemical switch and the measuring electrode, placing the biosensor in an environment suspected of containing a target material, contacting the biochemical switch to the suspected environment, and determining the presence of the target material.

23. A method of making a biosensor, the method comprising:

providing a biochemical switch having a hydrophilic film layer containing a recognition biomolecule, the recognition biomolecule having an ion channel blocker and a recognition moiety capable of specifically binding with a target agent, providing a hydrophobic gate membrane containing ion channels, providing a measuring device, said measuring device comprising a conductive measuring electrode and means for measuring a current surge between the biochemical switch and the measuring electrode, connecting the gate membrane to the measuring device, and connecting the biochemical switch with the gate membrane.

* * * * *